US011517901B2

(12) United States Patent
Lee et al.

(10) Patent No.: US 11,517,901 B2
(45) Date of Patent: Dec. 6, 2022

(54) HIGH-EFFICIENCY PARTICLE ENCAPSULATION IN DROPLETS WITH PARTICLE SPACING AND DOWNSTREAM DROPLET SORTING

(71) Applicant: THE REGENTS OF THE UNIVERSITY OF CALIFORNIA, Oakland, CA (US)

(72) Inventors: Abraham P. Lee, Irvine, CA (US); Gopakumar Kamalakshakurup, Irvine, CA (US); Mohammad Aghaamoo, Irvine, CA (US); Xuan Li, Irvine, CA (US); Gisela Lin, Irvine, CA (US); Xuhao Luo, Irvine, CA (US); Marzieh Ataei, Irvine, CA (US); Michelle A. Digman, Irvine, CA (US); Francesco Palomba, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 506 days.

(21) Appl. No.: 16/707,560

(22) Filed: Dec. 9, 2019

(65) Prior Publication Data
US 2020/0108393 A1  Apr. 9, 2020

Related U.S. Application Data

(63) Continuation-in-part of application No. PCT/US2019/053006, filed on Sep. 25, 2019, and a
(Continued)

(51) Int. Cl.
*B01L 3/00* (2006.01)
*C12N 11/00* (2006.01)
(Continued)

(52) U.S. Cl.
CPC ... *B01L 3/502784* (2013.01); *B01L 3/502715* (2013.01); *B01L 3/502746* (2013.01);
(Continued)

(58) Field of Classification Search
CPC ....... B01L 3/502784; B01L 2200/0673; B01L 3/502761; B01L 2200/0652;
(Continued)

(56) References Cited

U.S. PATENT DOCUMENTS 2,656,508 A   10/1953   Coulter
3,380,584 A    4/1968   Fulwyler
(Continued)

FOREIGN PATENT DOCUMENTS

GB          2395196 A         5/2004
WO    WO2007120240 A2        10/2007
(Continued)

OTHER PUBLICATIONS

International Search Report for PCT Application No. PCT/US18/56852 dated Jan. 11, 2019.
(Continued)

*Primary Examiner* — Dean Kwak
(74) *Attorney, Agent, or Firm* — Nguyen Tarbet LLC

(57) ABSTRACT

A passive, hydrodynamic technique implemented using a microfluidic device to perform co-encapsulation of samples in droplets and sorting of said droplets is described herein. The hydrodynamic technique utilizes laminar flows and high shear liquid-liquid interfaces at a microfluidic junction to encapsulate samples in the droplets. A sorting mechanism is implemented to separate sample droplets from empty droplets. This technique can achieve a one-one-one encapsulation efficiency of about 80% and can significantly improve the droplet sequencing and related applications in single cell genomics and proteomics.

13 Claims, 13 Drawing Sheets

Related U.S. Application Data continuation-in-part of application No. PCT/US2018/036952, filed on Jun. 11, 2018.

(60) Provisional application No. 62/736,163, filed on Sep. 25, 2018, provisional application No. 62/517,775, filed on Jun. 9, 2017.

(51) Int. Cl.
  G01N 15/10  (2006.01)
  G01N 15/14  (2006.01)
  G01N 21/64  (2006.01)
  G01N 35/08  (2006.01)

(52) U.S. Cl.
  CPC ........ *B01L 3/502761* (2013.01); *C12N 11/00* (2013.01); *G01N 15/10* (2013.01); *G01N 21/6408* (2013.01); *G01N 21/6458* (2013.01); *G01N 35/08* (2013.01); *B01L 2200/0652* (2013.01); *B01L 2300/06* (2013.01); *B01L 2300/0645* (2013.01); *B01L 2400/082* (2013.01)

(58) Field of Classification Search
  CPC ......... B01L 3/502746; B01L 3/502715; B01L 2300/0645; B01L 2400/082; G01N 2015/1006; G01N 15/1404; G01N 1/38; G01N 21/6408; G01N 21/6458; C12M 23/16; C12N 5/0012; C12N 11/00
  See application file for complete search history.

(56) References Cited

U.S. PATENT DOCUMENTS

| | | |
|---|---|---|
| 4,009,435 A | 2/1977 | Hogg |
| 5,465,582 A | 11/1995 | Bliss et al. |
| 7,595,195 B2 | 9/2009 | Lee et al. |
| 8,263,023 B2 | 9/2012 | Le Vot et al. |
| 8,365,311 B2 | 1/2013 | Nawarathna |
| 8,927,040 B2 | 1/2015 | Brand et al. |
| 9,176,504 B2 | 11/2015 | Chiou et al. |
| 2002/0182654 A1 | 12/2002 | Jing et al. |
| 2004/0234588 A1 | 11/2004 | Lu et al. |
| 2005/0015001 A1 | 1/2005 | Lec et al. |
| 2005/0106064 A1 | 5/2005 | Laurell et al. |
| 2005/0272039 A1 | 12/2005 | Yasuda |
| 2005/0272096 A1 | 12/2005 | Clague et al. |
| 2006/0051329 A1* | 3/2006 | Lee ................ B01F 25/433 435/440 |
| 2006/0177815 A1 | 8/2006 | Soh et al. |
| 2007/0264320 A1 | 11/2007 | Lee et al. |
| 2008/0038807 A1 | 2/2008 | Pommersheim |
| 2008/0241875 A1 | 10/2008 | Hwang et al. |
| 2009/0035838 A1 | 2/2009 | Quake et al. |
| 2009/0042310 A1 | 2/2009 | Ward et al. |
| 2009/0068170 A1 | 3/2009 | Weitz et al. |
| 2009/0075390 A1 | 3/2009 | Linder et al. |
| 2009/0181864 A1 | 7/2009 | Nguyen et al. |
| 2009/0286300 A1 | 11/2009 | Le Vot et al. |
| 2009/0298191 A1 | 12/2009 | Whitesides et al. |
| 2011/0059556 A1 | 3/2011 | Strey et al. |
| 2011/0086352 A1 | 4/2011 | Bashir et al. |
| 2011/0285042 A1 | 11/2011 | Viovy et al. |
| 2012/0034155 A1 | 2/2012 | Hyde et al. |
| 2012/0107912 A1 | 5/2012 | Hwang et al. |
| 2012/0196288 A1 | 8/2012 | Beer |
| 2013/0078163 A1 | 3/2013 | Chung et al. |
| 2013/0154671 A1 | 6/2013 | Lee et al. |
| 2013/0171628 A1 | 7/2013 | Di Carlo et al. |
| 2013/0210649 A1 | 8/2013 | McKnight et al. |
| 2014/0011291 A1 | 1/2014 | Patel et al. |
| 2014/0068797 A1 | 3/2014 | Doudna et al. |
| 2014/0076430 A1 | 3/2014 | Miller et al. |
| 2015/0018226 A1 | 1/2015 | Hansen et al. |
| 2016/0033378 A1 | 2/2016 | Husain et al. |
| 2016/0123858 A1 | 5/2016 | Kapur et al. |
| 2016/0202153 A1 | 7/2016 | Gadini et al. |
| 2017/0014449 A1 | 1/2017 | Bangera et al. |
| 2017/0128940 A1* | 5/2017 | Amini ............... B01L 3/502784 |
| 2017/0145169 A1 | 5/2017 | Oakey et al. |
| 2017/0183722 A1 | 6/2017 | Link |
| 2018/0030515 A1 | 2/2018 | Regev et al. |
| 2018/0078940 A1 | 3/2018 | Lee et al. |
| 2018/0135117 A1 | 5/2018 | Link |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.

J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.

X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.

Mazutis, L. et al., Lab on a Chip, vol. 9, pp. 2665-2672 (2009).

Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).

Marsh et al. Room temperature ionic liquids and their mixtures—a review. Fluid Phase Equilibria 219 (2004) 93-98.

Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.

Baret et al., "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.

Macosko et al., "Highly Parallel Genome-wide Expression Profiling of Individual Cells Using Nanoliter, Droplets," Cell, vol. 161, No. 5, pp. 1202-1214, May 2015.

International Search Report for PCT Application No. PCT/US18/36962 dated Aug. 30, 2018.

International Search Report for PCT Application No. PCT/US18/36952 dated Sep. 18, 2018.

Inexpensive Droplet-Based Microfluidic Platform. CIDAR lab. https://www.youtube.com/watch?v=aHvfEOlh_b4.

Kamalakshakurup et al. High-efficiency single cell encapsulation and size selective capture of cells in picoliter droplets based on hydrodynamic micro-vortices. Lab Chip, 2017, 17, 4324-4333.

Brouzes, Eric, et al. "Droplet microfluidic technology for single-cell high-throughput screening." Proceedings of the National Academy of Sciences 106.34 (2009): 14195-14200.

S. I. Rubinow and J. B. Keller, "The transverse force on a spinning sphere moving in a viscous fluid," J. Fluid Mech., vol. 11, No. 03, p. 447, Nov. 1961.

Murata et al., Electrochemical single-cell gene-expression assay combining dielectrophoretic manipulation with secreted alkaline phosphatase reporter system, 2009, Biosensors and Bioelectronics, 25, 913-919.

Stinson et al., Genes Expressed in the Male Gametophyte of Flowering Plants and Their Isolation, 1987, Plant Physiol., 83, 442-447.

(56) References Cited

OTHER PUBLICATIONS

International Search Report for PCT Application No. PCT/US2016/056683 dated Dec. 27, 2016.
International Search Report for PCT Application No. PCT/US18/55722 dated Feb. 6, 2019.
International Search Report for PCT Application No. PCT/US17/55984 dated Dec. 14, 2017.
Doria, Arlene et al., "Rapid blood plasma separation with air-liquid cavity acoustic transducers", 15th International conference on miniaturized systems for chemistry and life sciences, Oct. 2-6, 2011, pp. 1882-1884.
Lee, Abraham P. et al. , "Microfluidic air-liquid cavity acoustic transducers for on-chip integration of sample preparation and sample detection", Journal of laboratory automation, Dec. 2010, vol. 15, No. 6, pp. 449-454.
International Search Report Issued for PCT Application No. PCT/US2013/042735 dated Nov. 28, 2013.
Tovar, A. et al. Lateral Cavity Acoustic Transducer. Biomedical Engineering, University of California, Irvine, USA. Oct. 12, 2008. 1384-1386. Twelfth International Conference on Miniaturized Systems for Chemistry and Life Sciences. San Diego, California, USA.

\* cited by examiner

HIGH-EFFICIENCY PARTICLE ENCAPSULATION IN DROPLETS WITH PARTICLE SPACING AND DOWNSTREAM DROPLET SORTING

CROSS-REFERENCES TO RELATED APPLICATIONS

This application is a continuation-in-part and claims benefit of PCT/US2019/053006 filed Sep. 25, 2019, which claims benefit of U.S. Provisional Application No. 62/736, 163 filed Sep. 25, 2018, the specification(s) of which is/are incorporated herein in their entirety by reference.

This application is a continuation-in-part and claims benefit of PCT/US2018/036952 filed Jun. 11, 2018, which claims benefit of U.S. Provisional Application No. 62/517, 775 filed Jun. 9, 2017, the specification(s) of which is/are incorporated herein in their entirety by reference.

GOVERNMENT SUPPORT

The inventions were made with government support under Grant Nos. 1362165, 402521-21801 (KFS # FG19352), KFS0282527, and KFS0402521 awarded by the National Science Foundation, and Grant No. 2P41GM103540 awarded by NIH. The government may have certain rights in the inventions.

FIELD OF THE INVENTION

The present invention relates to microfluidic devices, namely, to encapsulation of samples in microdroplets and sorting of the microdroplets using droplet-based microfluidic devices.

BACKGROUND OF THE INVENTION

Precision cell and molecular platforms are needed to enable the efficient development of new medicines and better crops. Specifically, efficient quantification of single cell genotype, phenotype, and cell-cell interaction will address critical bottlenecks in business sectors such as the pharmaceutical and agricultural biotechnology industries. Current methods for single cell encapsulation in droplets at this scale are inefficient (~1%) and waste precious, costly materials. More importantly, many single cell analysis methods produce a mean response over a large population of cells, such that the cellular variance contributing to that response, where critical information lies, remains elusive.

Furthermore, metabolic single cell characterization allows a deeper understanding of subcellular functional and biochemical changes associated with healthy tissue development and the progression of numerous diseases. Identifying individual cells in a noninvasive, label-free manner is crucial for the detection of energy metabolism which will discriminate cell types and most importantly maintain cell viability for further analysis. In these studies cell lysis, common in genomic profiling assays, must be avoided. Thus, a versatile, microscale platform is required to address these shortcomings where a variety of single cell studies are enabled (genotype, phenotype, cell-cell interaction, metabolism, etc.) in a cost-effective, high throughput format.

Microfluidic devices and systems are configured to process (e.g., move, mix, separate) small volumes of fluid, typically in the range of picoliters to microliters. These microfluidic devices can be used for various applications including bio-chemical assays, drug discovery, etc. A class of microfluidic devices and systems includes microfluidic droplet generating and manipulating devices configured to manipulate discrete droplets. Droplet-based microfluidic devices can be configured to perform a variety of operations, such as transportation of droplets, storage of droplets, mixing of droplets, analysis of droplets, etc. For example, these devices can be used as microreactors to achieve controlled and rapid mixing of fluids and/or to synthesize droplets and encapsulate various biological entities for biomedicine and biotechnology applications.

Droplet-based single cell assays are based on the ability to encapsulate and confine single cells in individual droplets and enable high-efficiency genome wide expression profiling. Encapsulation of one-cell-one-bead in droplets is an essential operation for high-throughput screening of single cells and droplet sequencing. Most single cell encapsulations in droplets are performed randomly and are dictated by Poisson statistics. One of the current challenges in performing droplet sequencing (drop-seq) is achieving high efficiency one cell-one-bead encapsulation. It has been recently reported that for genome wide expression profiling, the encapsulation efficiency is as low as 0.1%, or 1 in 1000 droplets will have a cell therein. Another challenge is the ability to sort the cells once they have been encapsulated and indexed. Hence, there is a need for improved microfluidic device and method for encapsulation in single droplets and sorting thereof.

In the prior arts, WO2016040476A1 by Regev et al. discloses a single cell nucleic acid analysis by droplet based encapsulation and molecular bar coding. The droplets are used to co-encapsulate a unique bar-coded bead with a nucleic acid that can be identified. This technique relies on random bead-cell encapsulation which is dictated by Poisson distribution. Hence, the bead-cell encapsulation efficiency is very low. To load single cells and bar-coded beads into droplets with Poisson statistics, 100,000 to 10 million such beads are needed to bar-code about 10,000-100,000 cells.

US20120196288A1 of Beer teaches a non-contact method for isolating and sorting of droplets based on their content and their interaction with an applied electromagnetic field. The system provides an apparatus for generation of monodispersed droplets and subsequently sorting them using alternating current dielectrophoresis (AC-DEP).

US20140011291A1 of Patel et al. describes the development of a microfluidic actuator/device that can be used to manipulate biological and non-biological particles and cells. Using acoustic microstreaming generated by lateral cavity acoustic transducers (LCAT), particles/cells can be manipulated to cross streamlines for further processing downstream. This device has been demonstrated to sort particles/cells to different outlet channels.

In Baret et al., a highly-efficient microfluidic fluorescence-activated droplet sorter (FADS) combines the advantages of microtitre-plate screening and traditional fluorescence-activated cell sorting (FACS). Single cells are compartmentalized in emulsion droplets, which can be sorted using dielectrophoresis in a fluorescence-activated manner (as in FACS) at rates of up to 2000 droplets/second (J.C. Baret, et. al, "Fluorescence-activated droplet sorting (FADS): efficient microfluidic cell sorting based on enzymatic activity," Lab Chip. 2009 Jul. 7; 9(13):1850-8. doi: 10.1039/b902504a. Epub 2009 Apr. 23).

The present invention features two-step technique to achieve high efficiency cell indexing coupled with downstream sorting. In the first step, >30% cell encapsulation can be achieved by an interfacial shearing method utilizing laminar flows and high shear liquid-liquid interface at a microfluidic junction. A sorting module is incorporated as a second step to improve the encapsulation efficiency further, by up to about 80%, by removing empty droplets and/or droplets that do not contain the desired number of cells, indexing beads, or both. The present invention further incorporates particle spacing techniques and FLIM with the microfluidic device to increase encapsulation efficiency.

SUMMARY OF THE INVENTION

It is an objective of the present invention to provide for microfluidic devices and methods for encapsulating biomolecules in droplets and sorting said droplets. Embodiments of the invention are given in the dependent claims. Embodiments of the present invention can be freely combined with each other if they are not mutually exclusive.

In some aspects, one-cell-one-bead encapsulation in droplets is realized by an interfacial hydrodynamic technique that combines the effects of laminar flow and high shear liquid-liquid interfacial boundary. Beads, cells and aqueous phase introduced through upper, lower and middle inlets respectively, create distinct laminar flow streams at a junction into a combining channel. The flow rates at the three inlets are kept equal to prevent the bead/cell migration across the streamlines due to Magnus forces. The beads and cells self-assemble in a single file along the channel wall while moving toward the droplet generation junction. Upon reaching the droplet generation junction, the beads and cells get pulled from either side of the channel wall toward the symmetrical high shear interfaces into the droplet. The droplet diameter has to be large enough to accommodate one cell and one bead in it. This can be achieved by precisely tuning the dispersed phase pressure ($P_d$) to continuous phase pressure ($P_c$) ratio ($\varphi$). An encapsulation efficiency of about 30% can be achieved.

Various embodiments discussed herein comprise microfluidic devices that are configured to encapsulate single particle or cells with high throughput. Various embodiments of the microfluidic devices can be configured to encapsulate particles or cells with an encapsulation efficiency of about 30% or greater. In some embodiments, the encapsulation efficiency is maximized in the squeezing regime to near dripping regime, where $Ca<10^{-1}$, and $\varphi$ is about 0.5-1.0.

In one embodiment, for a high capillary number (Ca) regime with typically dripping formation of droplets, having cells in high concentration can induce stretching of the interfaces and the spacing of droplets (if thread is smaller than cell diameter). This will prevent doublets but not empty droplets. If thread is larger than cell diameter, then spacing controls the 1-1-1 encapsulation. As for low capillary number regime (i.e. the squeezing droplet formation), the inventors have found that it is critical to have droplets nominally the same size as the orifice. This enables a dynamic effect of cells entering the droplets, and also enabling breakoff of single cell encapsulations. The inventors have discovered that it is most efficient to operate in low concentration of cells and trap them before allowing them to be pulled into the droplets one by one as the droplets are squeezing through the orifice. Further still, the spacing of cells is not as straightforward and requires a frequency matching that is experimentally determined. For both high and low capillary numbers (Ca), downstream sorting can increase the purity of single cell encapsulated droplets. Thus, to further improve the efficiency, a sorting module was incorporated to sort out the empty droplets from the 1-1-1 droplets. The sorting mechanism can be used to sort droplets that do not contain the desired number of cell, indexing cells, or both. Examples of sorting mechanism include, but are not limited to, dielectrophoretic (DEP) sorting, lateral cavity acoustic transducer (LCAT) sorting, or fluorescence-lifetime imaging microscopy (FLIM). Once undesirable droplets are removed, the efficiency can be improved up to about 80% at the output.

In some aspects, the present invention includes a method of encapsulating one or more solid samples (e.g., biological material comprising cellular material, one or more cells, one or more particles, one or more beads, etc.) in a droplet of a fluid (e.g., water). The method may comprise flowing a dispersed phase fluid stream comprising a solid sample (e.g., a biological sample comprising cellular material or one or more cells) dispersed in a fluid (e.g., water) through a combining channel; controlling the flow rates of the flow stream to establish laminar flow through the combining channel; flowing a continuous phase fluid through a continuous phase channel that intersects the combining channel, the continuous phase fluid being immiscible with the dispersed phase fluid; controlling the flow rate of the continuous phase fluid to shear the laminar flow of the dispersed phase fluid stream; generating droplets encapsulating the solid sample in an output microfluidic channel; and sorting the droplets so as to separate the droplets with samples from empty droplets.

One of the unique inventive features of the present invention is the combination of high shear interfaces for droplet encapsulation and a sorting mechanism to sort the droplets. High shear interfaces between the continuous phase and dispersed phase fluid streams can be formed, which increases the encapsulation efficiency. Without wishing to limit the present invention to a particular mechanism or theory, laminar flow guides the particles/cells along the channel wall toward the high shear interface, and the high shear interface draws the cells or particles toward it at a higher velocity resulting in self-spacing of the cells, thereby reducing and even eliminating the possibility of doublets. The sorting mechanism can further concentrate the droplets specifically to droplets having the desired sample, thereby increasing the encapsulation efficiency.

When cells and beads are introduced to the microfluidic device inlet, they assume random positions, which can limit encapsulation efficiencies based on Poisson statistics. Thus, in some aspects, encapsulation efficiency may be increased through the integration of cell/bead focusing and spacing units to the droplet microfluidic platform. In one embodiment, the spacing unit is a microchannel patterned with alternating regions with herringbone structures and regions without. At the inlet, the cells/particles are randomly distributed and after flowing through a sequence of herringbone structures, the particles become focused in a specific streamline due to the pressure gradient created by the herringbone structure and the inertial force owing to the fluid's velocity. Hence, the present invention allows for higher efficiency, high throughput experimentation with single cells with less material waste, resulting in major savings in time and cost. The same technology can be used to pair a cell with a different cell in a droplet allowing for fundamental cell-cell communication studies. This technology may also make higher throughput non-invasive studies of cell-level responses of more cell types, as well as crop improvements and higher throughput and more efficient drug screening, possible with high efficiency and minimum sample waste, which is very advantageous when dealing with rare cells or stem cells.

Without wishing to limit the present invention, the integration of focusing/spacing unit would dramatically improve the efficiency of sample preparation for single cell genomics and proteomics. By exploiting passive hydrodynamic and hydrophoretic phenomena through the integration of herringbone structures inside particle introducing channels, the cells/particles can be guided, focused and regularly spaced prior to or after entering the combining channel, as opposed to entering in random initial positions, without adding to device complexity and cost. This approach may considerably improve the encapsulation efficiency and would potentially reduce multiple encapsulation incidents.

Another innovative aspect of the subject matter of this application is embodied in a microfluidic device comprising a combining channel configured to transport a dispersed phase fluid stream comprising a solid sample (e.g., a biological sample comprising cellular material or one or more cells) dispersed in a fluid (e.g., water); and continuous phase channels intersecting the combining channel to form an intersection region. Each continuous phase channel is configured to transport a continuous phase fluid stream. The intersection region is configured to open into an output microfluidic channel, which bifurcates into a collection channel and a waste channel. The microfluidic device also includes a fluid controller to control the flow rates of the fluid streams to generate droplets encapsulating the solid sample. The flow rate of the dispersed phase flow stream can be controlled to establish laminar flow, and the flow rate of the continuous phase fluid stream can be controlled to shear the laminar flow of the dispersed phase fluid stream in the intersection region, thus generating droplets that enter the output microfluidic channel through an orifice. The microfluidic device may further comprise a sorting module coupled to the output microfluidic channel. The sorting module is configured to direct the sample droplets into the collection channel, and to direct empty droplets into the waste channel.

The microfluidic devices and methods described herein are not limited to 1-1-1 encapsulation. In other embodiments, the microfluidic devices and methods may be used for encapsulating one cell in one droplet, i.e. 1-1 encapsulation. Another important advantage of the present invention is that it can be modified based on the desired application including single cell or bead encapsulation (1-1), and 1 cell-1 bead-1 droplet encapsulation or 1 cell-1 cell-1 droplet encapsulation (1-1-1) for different cell types and cell sizes.

According to other aspects, the present invention features 1-1 or 1-1-1 droplet-based encapsulation combined with phase fluorescence-lifetime imaging microscopy (FLIM) (i.e. single cell, cell-bead, or cell-cell encapsulation with phasor FLIM) for performing high efficiency cell identification, metabolic assessment, and genome-wide expression profiling of individual cells and the interaction between cells (cell signaling, cell secretions, etc.). Capture of specific proteins and antigens from single cells using functionalized beads is also possible. The combination of droplet-based cell encapsulation with phase FLIM technique may also enable higher throughput experimentation with single cells with less material waste, resulting in major savings in time and cost. By pairing a cell with a different cell in a droplet, fundamental cell-cell communications can be monitored. For example, the present invention may enable higher throughput non-invasive studies of cell-level responses of more cell types, including those from precious samples, to a wider variety of compounds and/or other cells, leading to new medicines, vaccines, and crop improvements (higher yield, better tolerance to drought, etc.).

In one embodiment, by implementing FLIM, single cell responses (i.e. secretions of cytokines, antibodies, changes in metabolic state, etc.) resulting from exposure to a library of chemical compounds and/or other cell types can be evaluated non-invasively and with cellular level granularity for the first time via the present invention. This device exploits microscale fluid dynamics and the optical properties of cells to produce unique, indexed optical signatures allowing a cell's response to be tracked at unprecedented sensitivities and fidelities.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1A:
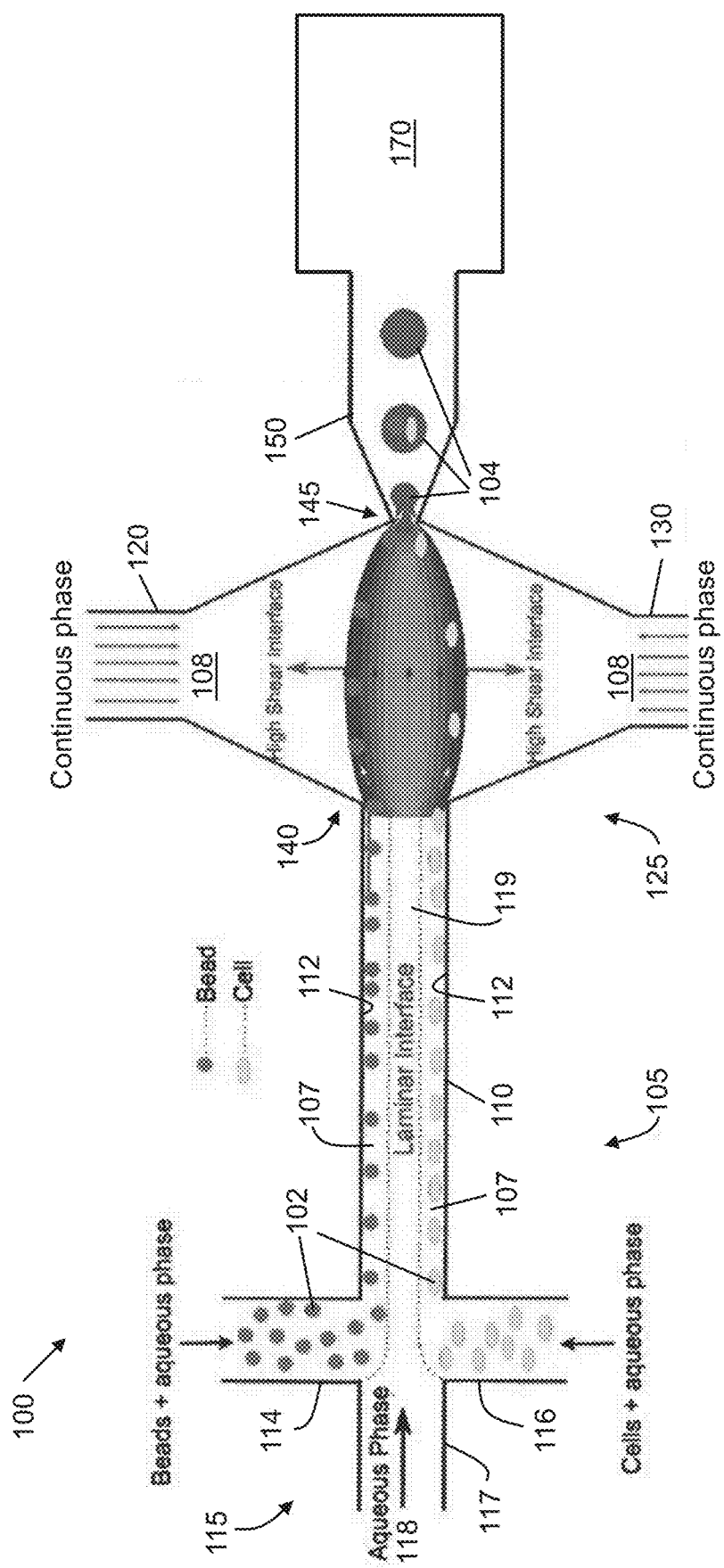
FIG. 1A shows an exemplary schematic of high efficiency cell indexing in one-cell-one-bead droplets (1-1-1), according to an embodiment of the present invention. Beads and cells introduced from upper and lower inlets self-assemble along the channel wall while moving toward high shear interfaces. At the droplet generation junction, both the beads and cells get pulled toward the high shear interface symmetrically from both the channel boundaries resulting in one-one-one encapsulation. A sorting module is incorporated downstream to sort out empty droplets from the bead-cell droplets.

Following lists elements corresponding to a particular element referred to herein:
100 microfluidic device
102 solid sample
104 droplet
106 dispersed phase fluid
107 flow stream
108 continuous phase fluid
109 high shear interface
110 combining channel
112 channel sidewall
114 first dispersed phase channel
116 second dispersed phase channel
117 aqueous phase channel
118 aqueous phase fluid
119 laminar interface stream
120 first continuous phase channel
130 second continuous phase channel
135 expansion-contraction regions
140 intersection region
145 droplet shearing junction
147 orifice
150 output channel
154 collection channel
156 waste channel
160 fluid flow controller
170 sorting module As used herein, the microfluidic devices employ fluid volumes on the scale of microliters ($10^{-6}$) to picoliters ($10^{-12}$) that are contained within sub-millimeter scale channels. The structural or functional features may be dimensioned on the order of mm-scale or less, preferably in the micron scale or less. For example, a diameter or width of a channel or a dimension of an intersection or junction may range from <0.1 μm to greater than 1000 μm. Alternatively or in addition, a length of a channel may range from 0.1 μm to greater than cm-scale. The microfluidic device may employ active or passive techniques for fluid transport and droplet production. Compared to the active approach, which fluid manipulation involves the use of micropumps and microvalves, the passive approach takes advantage of the characteristic flow field in microfluidics to control the interface and capillary instability, and consequently to produce droplets.

As used herein, the term "high shear interface" refers to a high velocity liquid-liquid interface formed between two immiscible liquids. Generally, the continuous phase flow rate is greater than the flow rate of the dispersed phase. For instance, the continuous phase flow rate may be about 2-5 times greater. At the aqueous-oil interface, the high continuous phase flow rate imparts the same velocity to the dispersed phase at the interface. Hence, the dispersed phase at the interface is at a higher velocity (shear) than the bulk. As used herein, the term "laminar flow" refers to flow of a fluid in layers that do not mix. One of ordinary skill in that art would understand that at lower Reynold's numbers (<10), a laminar flow is always established in the microfluidic channel. The fluid flows in parallel layers with no lateral mixing but with some minor diffusion.

As used herein, particles can be 1 cell and 1 barcoded bead to facilitate high efficiency single cell indexing (>30%), or both particles can be cells of different types to facilitate high fidelity cell-cell interaction studies. This type of encapsulation is termed "1-1-1 encapsulation." If both particles are the same cell type, high efficiency single cell encapsulation (>50%) can be achieved, termed "1-1 encapsulation."

As known to one of ordinary skill in the art, in a geometry-mediated regime, or squeezing regime, the droplet generation depends only on the size of the orifice and the flow rate ratio of the dispersed phase to the continuous phase flow rate, whereas interfacial tension and viscosity has no significant influence. The transition between the geometry-mediated regime to a dripping regime is dictated by the Capillary number (Ca), $$Ca = \frac{\mu \cdot v}{\sigma},$$

where $\mu$ is the viscosity, $v$ is the velocity of the continuous phase, and $\sigma$ is the interfacial tension between the two fluid phases. Generally, in the geometry-mediated regime, Ca is $<10^{-1}$. In the dripping regime, Ca may be $\geq 10^{-1}$ and interfacial tension and viscosity can predict the formation of droplets.

Samples for Encapsulation

In some embodiments, the samples for encapsulation may be microparticles. The microparticles may be beads. Examples of beads include, but are not limited to, polymer beads, bar-coded beads, functionalized beads, and magnetic beads. In some embodiments, the beads may have a size or dimension, such as a diameter or width, ranging from about 0.01 μm to about 20 μm.

In some other embodiments, the samples for encapsulation may be cells. Any particular cell type from any organism may be used in the methods and systems of the present invention. The cells may have a size or dimension, such as a diameter or width, ranging from about 0.1 μm to about 20 μm. In some embodiments, the cells may be wild type cells or genetically modified cells. In other embodiments, the cells may be cells harboring one or more mutations, healthy cells, stem cells, diseased or unhealthy cells, etc. For example, in some embodiments, the cells may be prokaryotic cells (e.g., bacteria, archaebacteria, etc.). In other embodiments, the cells may be eukaryotic cells such as single-celled eukaryotes, fungal cells (e.g. yeast, mold, etc.), animal cells, mammalian cells (e.g. cells from a human, non-human primate, rodent, rabbit, sheep, dog, cat, etc), and non-mammalian cells (e.g. cells from insects, reptiles, amphibians, birds, etc.).

In some embodiments, the cells used in the present invention may be other eukaryotic cells such as plant cells or algal cells. Non-limiting and non-exhaustive examples of plant cells include cells from corn, soybean, wheat, cotton, grass, flowering plants, fruit-bearing plants, trees, tuberous plants, potatoes, root plants, carrots, peanut, nuts, beans, legumes, and squashes. It is to be understood that the term "plant cell" encompasses all types and stages of plant cells and is not limited to the aforementioned examples. Non-limiting and non-exhaustive examples of algal cells include cells from *Chlorella* sp., *Nannochloropsis* sp, and *Botryococcus* sp. It is to be understood that the term "algal cell" encompasses all types of algal cells and is not limited to the aforementioned examples. One of the distinguishing characteristics that plant and algal cells have over animal cells is a cell wall that surrounds a cell membrane to provide rigidity, strength, and structure to the cell. The cell wall may be comprised of polysaccharides including cellulose, hemicellulose, and pectin. Similar to plant and algal cells, the fungal cells also have a cell wall, which may be comprised of polysaccharides including glucans, mannans, and chitin.

In other embodiments, the cells used in the present invention may be protoplasts, which are intact plant, bacterial or fungal cells that had its cell wall completely or partially removed using either mechanical or enzymatic means.

In yet other embodiments, the cells used in the present invention may be a tetrad. The term "tetrad" is used to herein to refer to a single structure comprised of four individual physically attached components. A "microspore" is an individual haploid structure produced from diploid sporogenous cells (e.g., microsporoyte, pollen mother cell, or meiocyte) following meiosis. A microspore tetrad refers to four individual physically attached microspores. A "pollen grain" is a mature gametophyte containing vegetative (non-reproductive) cells and a generative (reproductive) cell. A pollen tetrad refers to four individual physically attached pollen grains.

In some preferred embodiments, the samples may be comprised solely of cells. In other preferred embodiments, the samples may comprise a combination of cells and microparticles. For example, the samples that are encapsulated in a droplet may comprise a cell and a bead.

Droplet Screening

In some aspects, droplets are generated in microfluidic devices by flowing a first liquid (e.g., water) through a first channel and a second liquid (e.g., oil) that is immiscible with the first liquid through channels intersecting the first channel. The first liquid flowing through the first channel (e.g., water) is broken up to form discrete droplets as a result of shear forces from the second liquid. The size of the generated first liquid droplets generated can depend on a variety of factors including velocity of the second liquid. For example, as the velocity of the second liquid is increased, the size of the first liquid droplets is reduced.

Referring now to FIG. 1A-3B, in some embodiments, the present invention provides a microfluidic device (100) for screening droplets (104). The device may comprise a first microfluidic channel network (105) having a first fluid (106), comprising dispersed sample (102), flowing therein at a first flow rate ($v_d$), a second microfluidic channel network (125) having a second fluid (108) flowing therein at a second flow rate ($v_c$), an intersection region (140) formed by the second microfluidic channel network (125) intersecting the first microfluidic channel network (105), and an output channel (150) divided into a plurality of collection channels (154). Preferably, a droplet shearing junction (145) is formed within the intersection region (140) as the second fluid stream (108) intersects the first fluid (106), and fluidly couples the intersection region (140) to the output channel (150). A sorting module (170) may be operatively coupled to the output channel (150) and disposed at or near the divide of the output channel (150). The sorting module (170) is configured to direct the droplets into a specific collection channel (154) based on droplet content.

In some embodiments, the device may further include a fluid flow controller (160) configured to perform operations comprising adjusting $v_d$, $v_c$, or both such that the second fluid stream (108) forms a high shear interface (109) with the first fluid (106) and the solid samples (102) are drawn to the high shear interface (109), and adjusting $v_d$, $v_c$, or both to generate droplets (104) at the droplet shearing junction (145), which are outputted into the output channel (150). Preferably, a plurality of said droplets (104) is substantially sized to encapsulate at least one sample (102) or co-encapsulate at least two different samples (102).

Figure 7A:
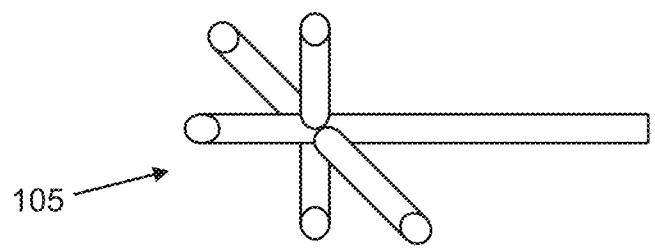
FIGS. 7A-7B show non-limiting alternate embodiments of inlet channels of the first microfluidic network in the microfluidic device.
Figure 7B:
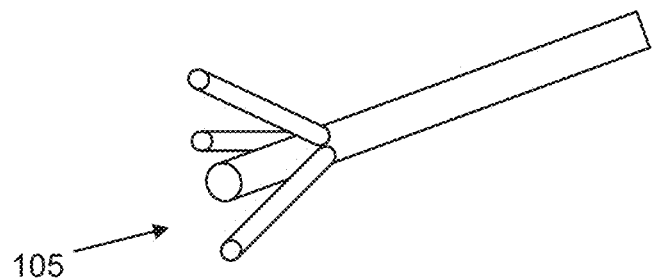
Figure 8A:
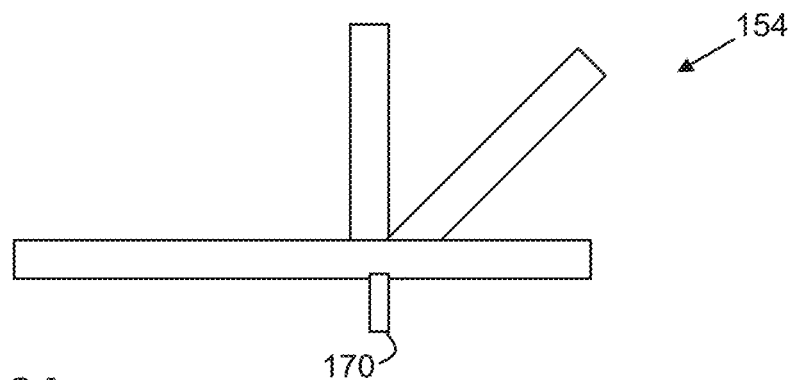
FIGS. 8A-8B show non-limiting alternate embodiments of the sorting module in the microfluidic device.
Figure 8B:
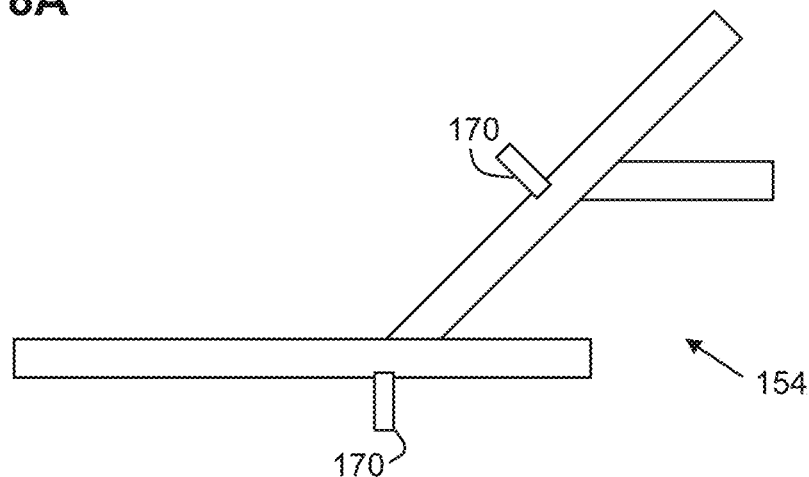
Figure 9:
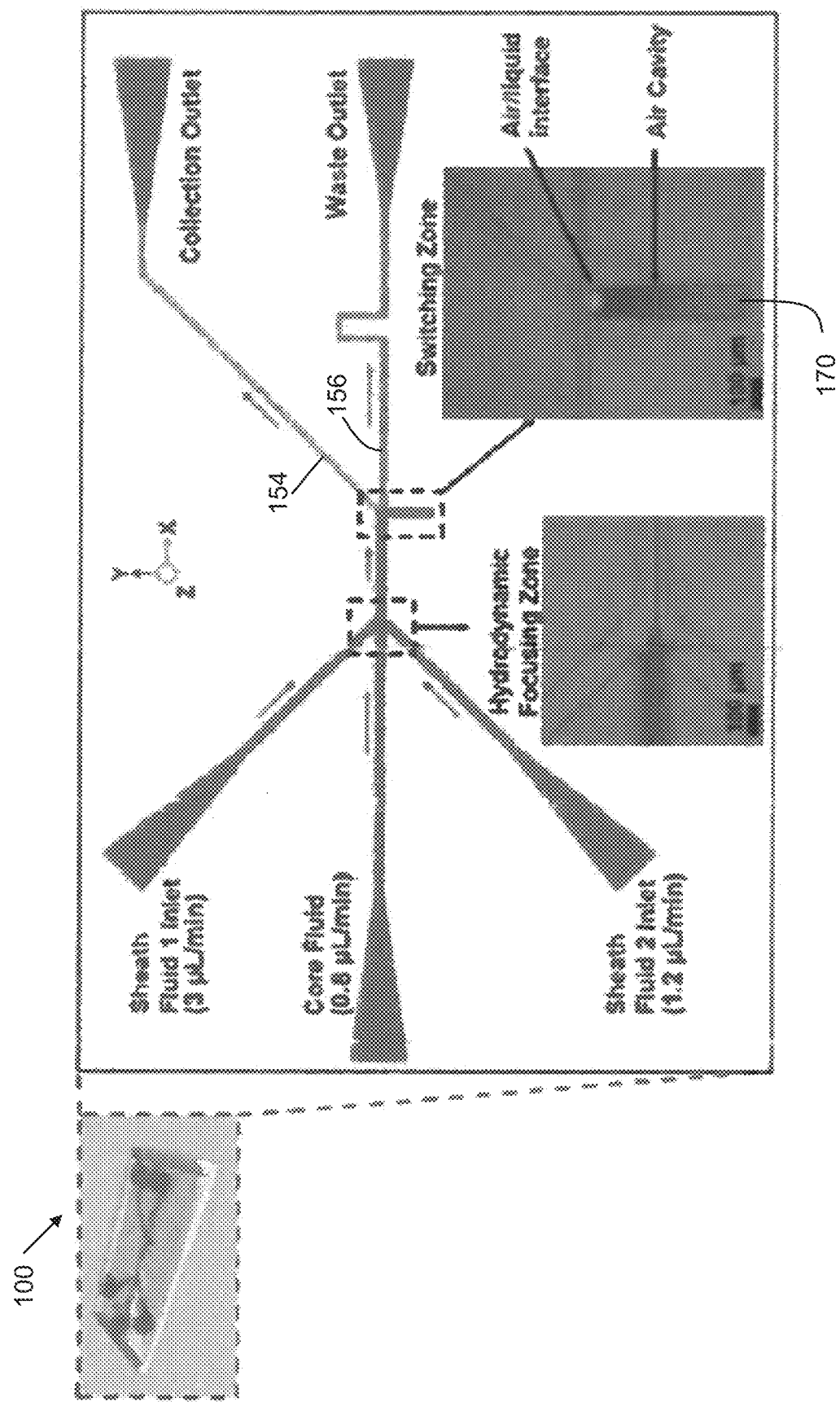
FIG. 9 shows a lateral cavity acoustic transducer (LCAT) switching device schematic. Three inlet channels enable asymmetrical hydrodynamic focusing of cell and particles as they flow through the core combing channel. A bifurcating outlet channel geometry at the back edge of the LCAT enables switching of cells and particles. When the LCAT is in an ON state, the cells and particles are deflected into the collection channel.
Figure 10A:
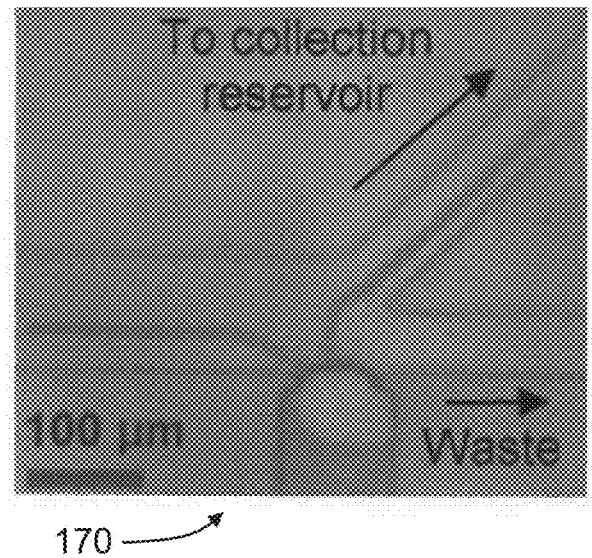
FIGS. 10A-10C show micrographs of typical pathlines observed for an LCAT ON time of 3.1 ms (FIGS. 10A-10B) and 1.6 ms (FIG. 10). The switching zone of the LCAT can be controlled by varying the actuation time. If the LCAT is not "on", then the beads flow into the waste channel. This LCAT mechanism in a non-limiting embodiment for droplet sorting.
Figure 10B:
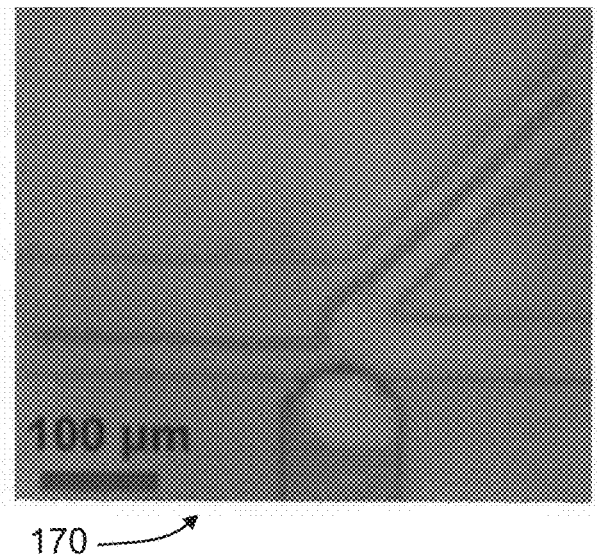
Figure 10C:
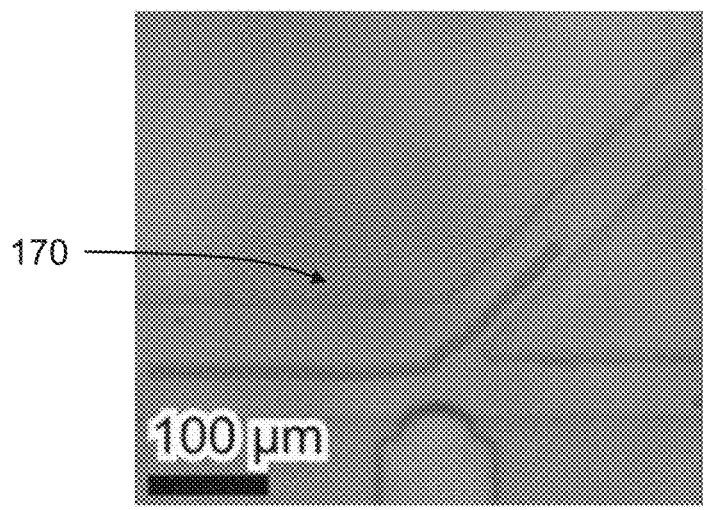

In one embodiments, the first microfluidic channel network (105) may comprise a plurality of inlet channels (115) merging into a combining channel (110). The first microfluidic channel network (105) may comprise 2-6 inlet channels (115). For example, as shown in FIG. 1A, the first microfluidic channel network (105) may include 3 inlet channels. In alternative embodiments, as shown in FIGS. 7A and 7B, the first microfluidic channel network (105) may comprise 4 or 5 inlet channels. In some embodiments, each inlet channel (115) contains one flow streams (107) that flows into the combining channel (110), thereby forming the first fluid (106) may comprise a plurality of flow streams (107). Preferably, the flow rate of the flow streams creates laminar flow in the combining channel (110).

In other embodiments, the second microfluidic channel network (125) may comprise a first continuous phase channel (120), and a second continuous phase channel (130). A portion of the first continuous phase channel (120) may be disposed on one side of the combining channel and a portion of the second continuous phase channel (130) may be disposed on an opposite side of the combining channel. The portions of the first and second continuous phase channels are configured to intersect the intersection region (140).

In some embodiments, the flow stream (107) through the inlet channels (115) may comprise dispersed samples (102) or an aqueous phase fluid (118). For example, one or two inlet channels may have flow streams with dispersed samples and another inlet channel introduces aqueous phase fluid to the combining channel. In some preferred embodiments, the samples (102) assemble near a sidewall (112) of the combining channel as they flow towards the intersection region (140). In one embodiment, the aqueous phase fluid (118) flows in the combining channel (110) such that the aqueous phase fluid (118) forms a laminar interface stream (119) between the dispersed sample flow streams. Non-limiting examples of the aqueous phase fluid (118) include water, lysis buffer, and/or other lysis reagents.

According to other embodiments, the microfluidic device may be used in a method for screening droplets (104). The method may comprise flowing a first fluid (106), comprising dispersed samples (102), at a first flow rate ($v_d$) through a first microfluidic channel network (105) and into an intersection region (140), and co-flowing a second fluid (108) through a second microfluidic channel network (125) at a second flow rate ($v_c$). The flow rates, $v_d$, $v_c$, or both, are adjusted such that the second fluid stream (108) forms a high shear interface (109) with the first fluid (106), and the solid samples (102) are drawn to the high shear interface (109). In order to generate droplets, $v_d$, $v_c$, or both are further adjusted to generate droplets (104) at the droplet shearing junction (145), which are outputted into an output channel (150). Preferably, a plurality of said droplets is substantially sized to encapsulate at least one sample or co-encapsulate at least two different samples. The method continues by sorting the sample droplets using a sorting module (170) operatively coupled to the output channel (150). The sorting module (170) can direct the droplets into a specific collection channel (154) based on droplet content.

In some embodiments, the dispersed samples (102) may be either cells or particles. A shown in FIGS. 2A and 3A, one sample (102) can be encapsulated in one droplet (104). In some other embodiments, the dispersed samples (102) may comprise cells, particles, or a combination thereof. For example, at least two different samples (102), e.g. cell-cell or cell-bead, are encapsulated in one droplet (104).

As shown in FIG. 1A, the dispersed samples (102) may comprise a plurality of cells flowing in one of the flow streams (107) and a plurality of particles flowing in another flow stream (107). When flowing through the combining channel (110), laminar flow causes the cells to assemble near the sidewall (112a) and the particles to assemble near an opposing sidewall (112b). At the intersection region (140), the cells are drawn to one high shear interface (109a) and the particles are drawn to an opposing high shear interface (109b), thus one cell and one particle are co-encapsulated in one droplet (104) as said droplet (104) is formed at the droplet shearing junction (145).

As another example, one cell and one particle comprising a bar-coded bead can be encapsulated in one droplet (104). Due to the high costs of lysis reagents, it may be economical to produce lysis reagents in bead form, such as hydrogel beads, and encapsulate a lysis bead with a cell in one droplet. In yet another example, the dispersed samples may suitable for cell transfection. For instance, one cell, one particle comprising a transfection molecule, and one particle comprising a transfection reagent can be encapsulated in one droplet. Nucleic acid, e.g., DNA or RNA, is the most commonly transfected molecule. However, the present invention is not limited to transfection of DNA or RNA. In some embodiments, the transfection molecule is DNA, RNA, Cas9 nuclease, a protein, a carbohydrate, a small molecule (e.g., a drug), the like, or a combination thereof. Non-limiting examples of transfection reagents include cationic lipids, such as glycerol derived lipids, cholesterol derived lipids, pyridine derived lipids, malonic acid derived lipids, Lipofectamine®, poly-l-lysine (PLL), polyethyleneimine (PEI), Lipojet™, and LipoD293™, etc.

In accordance with the embodiments described herein, the methods and microfluidic devices of the present invention can encapsulate and sort droplets that are suitable for droplet sequencing (Drop-seq) and RNA sequencing (RNA-seq). In some embodiments, Drop-seq is a single-cell sequencing method using a microfluidic device to encapsulate droplets containing a single cell, lysis buffer, and a microbead containing bar-coded primers. For example, a single-cell suspension is prepared from a source of interest (e.g. cancer cells), bar-coded primers are prepared as bar-coded beads, and each cell is individually co-encapsulated with a distinctly bar-coded bead in a droplet. The sample droplets co-encapsulating a cell, lysis buffer, and a bar-coded bead are sorted by the sorting module (170) for downstream RNA sequencing. Following encapsulation, cells in the droplets are lysed to release their mRNAs, which then hybridize to the primers. The droplets are pooled and broken to collect the bar-coded mRNA beads. The mRNAs are then reverse-transcribed into cDNAs, which are PCR amplified to produce a cDNA library for sequencing.

According to another embodiment, the method of the present invention may include encapsulating a solid sample (102) in a droplet (104). The method of encapsulation may comprise flowing a first fluid (106) through a first microfluidic channel (110) at a first flow rate ($v_d$) such that flow of the first fluid is laminar, and co-flowing a second fluid (108) through each of a second microfluidic channel (120) and a third microfluidic channel (130) at a second flow rate ($v_c$). In one embodiment, the first fluid (106) may comprise at least two flow streams (107). One or both of said flow streams (107) may comprise dispersed solid samples (102) that self-assemble near a sidewall (112) of the first microfluidic channel while flowing towards an intersection region (140). The second and third microfluidic channels (120, 130) can intersect the first microfluidic channel (110) at the intersection region (140) such that the second fluid streams (108) intersect the first fluid (106) and merge to form a droplet shearing junction (145) within the intersection region (140). In some embodiments, the method further comprises adjusting $v_d$, $v_c$, or both such that each of the second fluid streams (108) forms a high shear interface (109) with the first fluid (106), and the solid samples (102) are drawn to the high shear interface (109), and generating droplets (104) at the droplet shearing junction (145). The droplets (104) are then outputted into an output channel (150). In some embodiments, a plurality of said droplets is substantially sized to encapsulate one solid sample or co-encapsulate two different solid samples.

In further embodiments, the method includes sorting the sample droplets from empty droplets using a sorting module (170) operatively coupled to the output channel (150), which is bifurcated into a collection channel (154) and a waste channel (156). Preferably, the sorting module (170) can direct the sample droplets (e.g. droplets encapsulating samples) into a collection channel (154), and direct empty droplets into the waste channel (156).

According to some embodiments, the method for screening microfluidic droplets (104), including encapsulating a solid sample (102) in a droplet (104), may comprise providing a microfluidic device (100). In some embodiments, the microfluidic device (100) may comprise a combining channel (110), a first continuous phase channel (120) having a portion thereof disposed on one side of the combining channel, and a second continuous phase channel (130) having a portion thereof disposed on an opposite side of the combining channel. The device may further include an output channel (150) fluidly coupled to the intersection region (140) and a sorting module (170) operatively coupled to the output channel (150). Preferably, the output channel (150) is bifurcated into a collection channel (154) and a waste channel (156). The sorting module (170) may be disposed at or near the bifurcation of the output channel (150). For instance, the sorting module (170) may be disposed at an exterior wall of the output channel.

In some embodiments, the portions of the first and second continuous phase channels can intersect at a terminal end of the combining channel to form an intersection region (140) to which the output channel (150) is fluidly coupled thereto. In one embodiment, the portions of the first and second continuous phase channels can intersect the combining channel (110) orthogonally such that the continuous phase channels and combining channel form a T-junction. Alternatively, the continuous phase channels can intersect the combining channel (110) at an acute angle such that the continuous phase channels and output channel form a Y-junction.

In some embodiments, the microfluidic device (100) may further comprise a first dispersed phase channel (114) comprising one of the flow streams (107) forming the dispersed phase fluid (106), and a second dispersed phase channel (116) comprising the other flow stream (107). The first and second dispersed phase channels (114, 116) can merge to form the combining channel (110). In other embodiments, the microfluidic device (100) may further comprise an aqueous phase channel (117) intersecting with the first and second dispersed phase channels (114, 116). The aqueous phase channel (117) may comprise aqueous phase fluid (118), which flows in the combining channel (110) such that the aqueous phase fluid (118) forms a laminar interface stream (119) between the two flow streams (107).

In other embodiments, the device (100) may further comprise a fluid flow controller (160) configured to perform operations. These operation can include adjusting $v_d$ of the dispersed phase fluid to establish laminar flow in the combining channel (110) such that the solid samples (102) assemble near a sidewall (112) of the combining channel while flowing towards the intersection region (140), adjusting $v_d$, $v_c$, or both such that each continuous phase fluid stream (108) forms a high shear interface (109) with the dispersed phase fluid (106) at the intersection region (140) and the solid samples (102) are drawn to the high shear interface (109) while flowing through the intersection region (140), and adjusting $v_d$, $v_c$, or both to generate droplets (104) at the droplet shearing junction (145). Preferably, a plurality of said droplets (104) is substantially sized to encapsulate at least one solid sample (102). In one embodiment, the flow in the microfluidic device (100) and adjustment of the flow rates may be pressure-driven. Preferably, the microfluidic device (100) utilizes passive techniques to control fluid flow.

In various embodiments, the width of the various microfluidic channels (e.g., the first and second dispersed phase and aqueous phase channels (114, 116, 117); the combining channel (110); and the continuous phase channels (120, 130)) can range from about 25 μm to about 75 μm. For examples, the width of the various microfluidic channels can be in a range between about 30 μm to about 60 μm.

In other embodiments, a width and/or length of the intersection region can be about 3-6 times the width of the various microfluidic channels (e.g., the combining channel, the first continuous phase channel, or the second continuous phase channel). For example, the width of the intersection region may be about 150 μm, which is about three times the width of a 50 μm incoming microfluidic channel. In another embodiment, the length of the intersection region may be about 200 μm, which is about four times the width of a 50 μm incoming microfluidic channels.

In some embodiments, the width of the orifice may be about 5-40 μm. For example, in one embodiments, the width of the orifice may be about 5-15 μm, about 10-20 μm, about 20-30 μm, or about 30-40 μm. In other embodiments, the width of the output channel may widen from the width of the orifice to a maximum width. The maximum width of the output channel can be about 2-10 times the width of the orifice. For example, for a 30 μm orifice, the output channel widens from a minimum width of 30 μm to a maximum width of about 120 μm. In further embodiments, the width of the output channel may be reduced after reaching its maximum. In some embodiments, the output channel splits into two channels, the collection channel and the waste channel. The width of the collection channel and the waste channel can range from about 25 μm to about 75 μm and are not necessarily the same widths.

Consistent with the embodiments described above, an exemplary implementation of the method may comprise flowing a dispersed phase fluid (106) through the combining channel (110) at a first flow rate ($v_d$), and adjusting $v_d$ of the dispersed phase fluid (106) to establish laminar flow in the combining channel (110) such that the solid samples (102) assemble near a sidewall (112) of the combining channel while flowing towards the intersection region (140). In one embodiment, the dispersed phase fluid (106) may comprise at least two flow streams (107), with one or both of the flow streams (107) having dispersed solid samples (102). Continuous phase fluid streams (108) co-flow through each of the first and second continuous phase channels (120, 130) at a second flow rate ($v_c$). The continuous phase fluid streams (108) can intersect the dispersed phase fluid (106) at the intersection region (140) such that a droplet shearing junction (145) is formed within the intersection region (140) as the continuous phase fluid streams (108) merge with the dispersed phase fluid (106). The droplet shearing junction (145) can comprise an orifice (147) that fluidly couples the output channel (150) to the intersection region (140). The method continues with adjusting $v_d$, $v_c$, or both such that each continuous phase fluid stream (108) forms a high shear interface (109) with the dispersed phase fluid (106) at the intersection region (140). The solid samples (102) are drawn to the high shear interface (109) while flowing through the intersection region (140). Preferably, $v_d$, $v_c$, or both are further adjusted to generate droplets (104), which are then outputted into the output channel (150). In some embodiments, at least 30% of the generated droplets (104) may be substantially sized to encapsulate at least one solid sample (102). All droplets flow through the output channel and approach the bifurcation point of the output channel. The sample droplets are then sorted or separated from empty droplets using the sorting module (170). Preferably, the sorting module (170) can direct the sample droplets into the collection channel (154), and direct empty droplets into the waste channel (156).

In one embodiment, the method and microfluidic device can be adapted to co-encapsulate two different samples in one droplet. For example, the dispersed solid samples (102) may comprise a plurality of cells flowing in one of the flow streams (107), and a plurality of particles flowing in the other flow stream (107). When flowing through the combining channel (110), laminar flow of the dispersed phase fluid causes the cells to assemble near the sidewall (112a) and the particles to assemble near an opposing sidewall (112b). At the intersection region (140), the cells are drawn to one high shear interface (109a) and the particles are drawn to the other high shear interface (109b), thereby enabling one cell and one particle to be co-encapsulated in one droplet (104) as said droplet (104) is formed at the droplet shearing junction (145). The droplet (104) co-encapsulating the one cell and one particle can then be released from the orifice (147) into the output channel (150).

In another embodiment, as shown in FIGS. 2A-3B, the method and microfluidic device can be adapted to encapsulate a single sample in one droplet. The dispersed solid samples (102) may comprise either cells or particles. The cells or particles enter the combining channel (110) from one or both of the first and second dispersed phase channels, and one solid cell or particle (102) is encapsulated as the droplet (104) is formed at the droplet shearing junction (145). The droplet (104) encapsulating the one solid sample (102) is released from the orifice (147) into the output channel (150).

Microfluidic droplet generators utilizing the droplet generation methods described herein can be used to compartmentalize or encapsulate a single cell or a bead comprising single cell, cellular material or some other biological material in a single water droplet. Droplets encapsulating a single cell or bead can be useful for single cell assays of cells (e.g., cancer cells or immune cells) that exhibit biological heterogeneity for which assays that provide a population average may be insufficient. Encapsulation of a single cell (one cell) and/or a single bead (one-bead) in a single droplet can be useful for high-throughput screening of single cell. As previously described of prior technologies, the efficiency of encapsulating a single cell (one cell) and/or a single bead (one-bead) in a single droplet can be as low as 0.1%, i.e. 1 in 1000 droplets may have a single cell (one cell) and/or a single bead (one-bead) while the remaining droplets may have no cells and/or beads or have more than one cell and/or one bead. Without wishing to limit the present invention, this application provides a passive, hydrodynamic technique which can achieve a 'one-one-one' (one cell and/or one bead in one droplet) encapsulation efficiency of 30% or higher, which could significantly improve the biomolecular capture efficiency of various bead-based single cell assays.

The device can be configured to encapsulate one cell and/or one bead in a single droplet of a fluid (e.g., water) by the combined effect of laminar flow and the high shear liquid-liquid interfacial boundary. In the illustrated device of FIG. 1A, a first fluid stream comprising a first solid sample (e.g., cells or cellular material) dispersed in a first fluid (e.g., water) is introduced through a first incoming microfluidic channel and a second fluid stream comprising a second solid sample (e.g., beads or particles) dispersed in the first fluid (e.g., water) is introduced through the second incoming microfluidic channel. A third fluid stream comprising the first fluid (e.g., water) is introduced through the third incoming microfluidic channel. The first, second and third flow streams, collectively referred to as a dispersed phase fluid stream, flow into the combining channel.

In some embodiments, the velocities of the first, second, and third flow streams can be adjusted such that laminar flow is established in the combining channel. For example, the flow rates of the first, second and third flow streams can be equal to each other such that laminar flow is established in the combining channel. By maintaining equal flow rates in the three incoming microfluidic channels, bead/cell migration across the streamlines due to Magnus force can be prevented. The first and the second fluid streams in the combining channel can be separated by a laminar interface as a result of the laminar flow. The constituents of the first solid sample (e.g., cells or cellular material) self-assemble on one side of the laminar interface and the constituents of the second solid sample (e.g., particles or beads) self-assemble on another side of the laminar interface. For example, beads or particles self-assemble in a single row along a channel wall of the combining channel adjacent to the incoming microfluidic channel of the bead or particles, and cells self-assemble in a single row along the opposite channel wall of the combining channel adjacent to the incoming microfluidic channel of the cells.

Figure 1B:
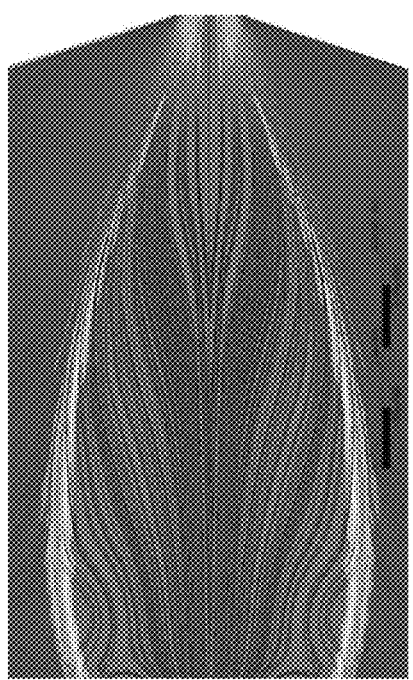
FIG. 1B shows an enlarged schematic of the encapsulation process using interfacial shearing (left), and a fluid dynamic model (CFD) of interfacial shearing (right).

The laminar flow of the dispersed phase fluid stream enters the intersection region. In the intersection region, the flow rate of the continuous phase fluid streams can be adjusted to create a high shear interface between the laminar flow of the dispersed phase fluid stream. Cells in the first flow stream and the beads or particles in the second flow stream are pulled towards the high shear interface as shown in FIG. 1B. The flow rates of the dispersed phase fluid stream and the continuous phase fluid streams can be adjusted to generate droplets having a droplet size large enough to encapsulate a single cell from the first flow stream and a single bead/particle from the second fluid stream. The size of the droplet can depend on the capillary number, $Ca=\mu V/\sigma$, where $\mu$ is the viscosity of the continuous phase comprising the second fluid, V is the superficial velocity (flow rate) of the continuous phase comprising the second fluid, and $\sigma$ is the equilibrium surface tension between the continuous phase and the dispersed phase fluid streams. To generate droplets having an appropriate size to encapsulate a single cell and/or single bead, the capillary number can be in the range of about 0.01 and about 1 (e.g., about 0.1). In various embodiments, the velocity of the continuous phase fluid streams can be about 2-10 times greater that the velocity of the dispersed phase fluid stream.

The droplet size can also be controlled by controlling the pressure ratio between the dispersed phase fluid stream and the continuous phase fluid stream. In various embodiments, a droplet encapsulating a single cell and a single bead/particle can be achieved by controlling the pressure ratio ($\varphi$) and/or the flow rate ratio between the dispersed phase and the continuous phase. In some embodiments, the pressure ratio and/or the flow rate ratio between the dispersed phase and the continuous phase may be about 0.1 to about 0.5 (e.g., about 0.3) in order to maximize encapsulation efficiency. Depending on the pressure ratio and/or the flow rate ratio, the generated droplets can be configured to have a diameter of about 20 μm to about 100 μm to match the size and/or concentration of the incoming cells and/or beads.

In various embodiments, the height of the various microfluidic channels is less than twice the diameter of the solid samples (e.g., cells, beads, particles, etc.) that are configured to be dispersed in dispersed phase fluid. Restricting the height of the various microfluidic channels to be less than twice the diameter of the solid samples can advantageously reduce the chance that the solid samples roll over each other and/or stack over each other.

Figure 1D:
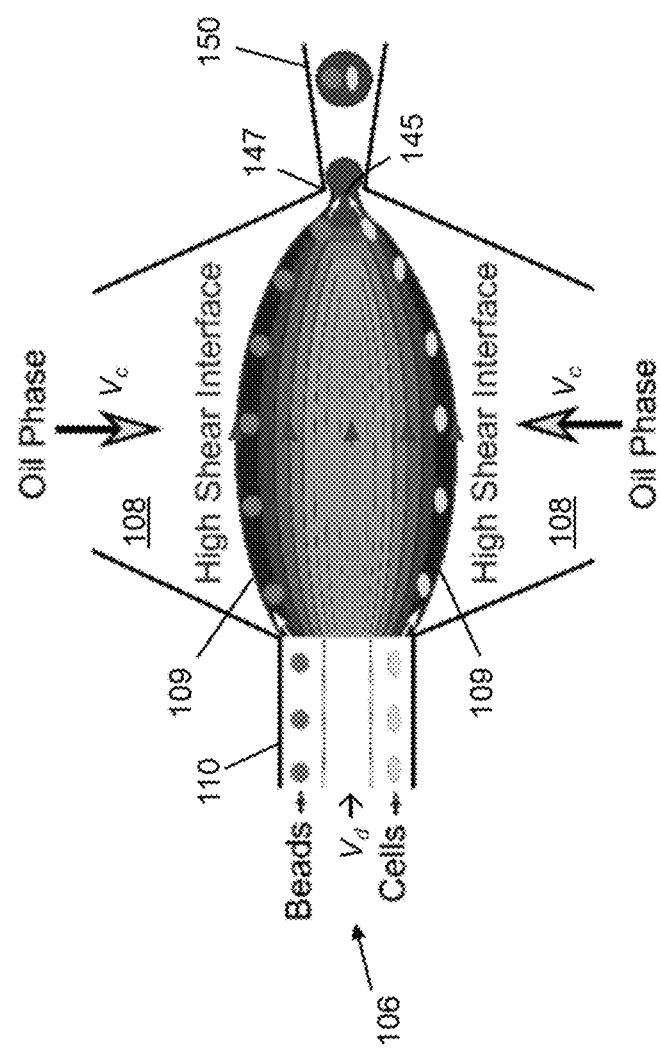
FIG. 1D shows the one cell-one bead encapsulation in droplets. The encircled droplets indicate the 1-1-1 droplets.
Figure 1D:
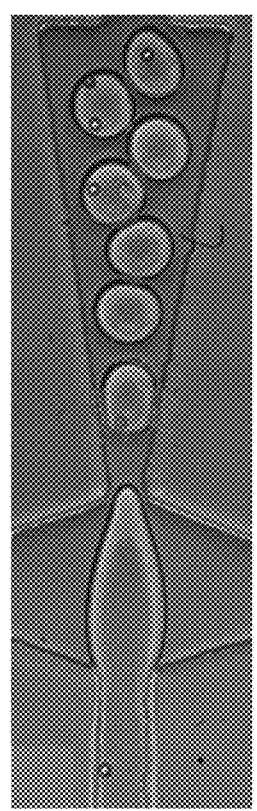
Figure 1C:
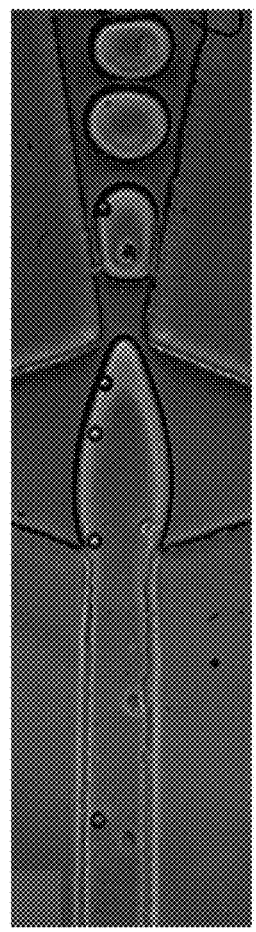
FIG. 1C shows the 10 µm beads self-assemble along the top channel wall while Hela cells align along the bottom wall.

In an exemplary embodiment, FIG. 1C depicts the self-assembly of 10 μm beads along the channel wall and the self-assembly of the Hela cells along the opposing channel wall. FIG. 1D demonstrates the droplets encapsulating a single 10 micron particle/bead and a single Hela cell.

Figure 2A:
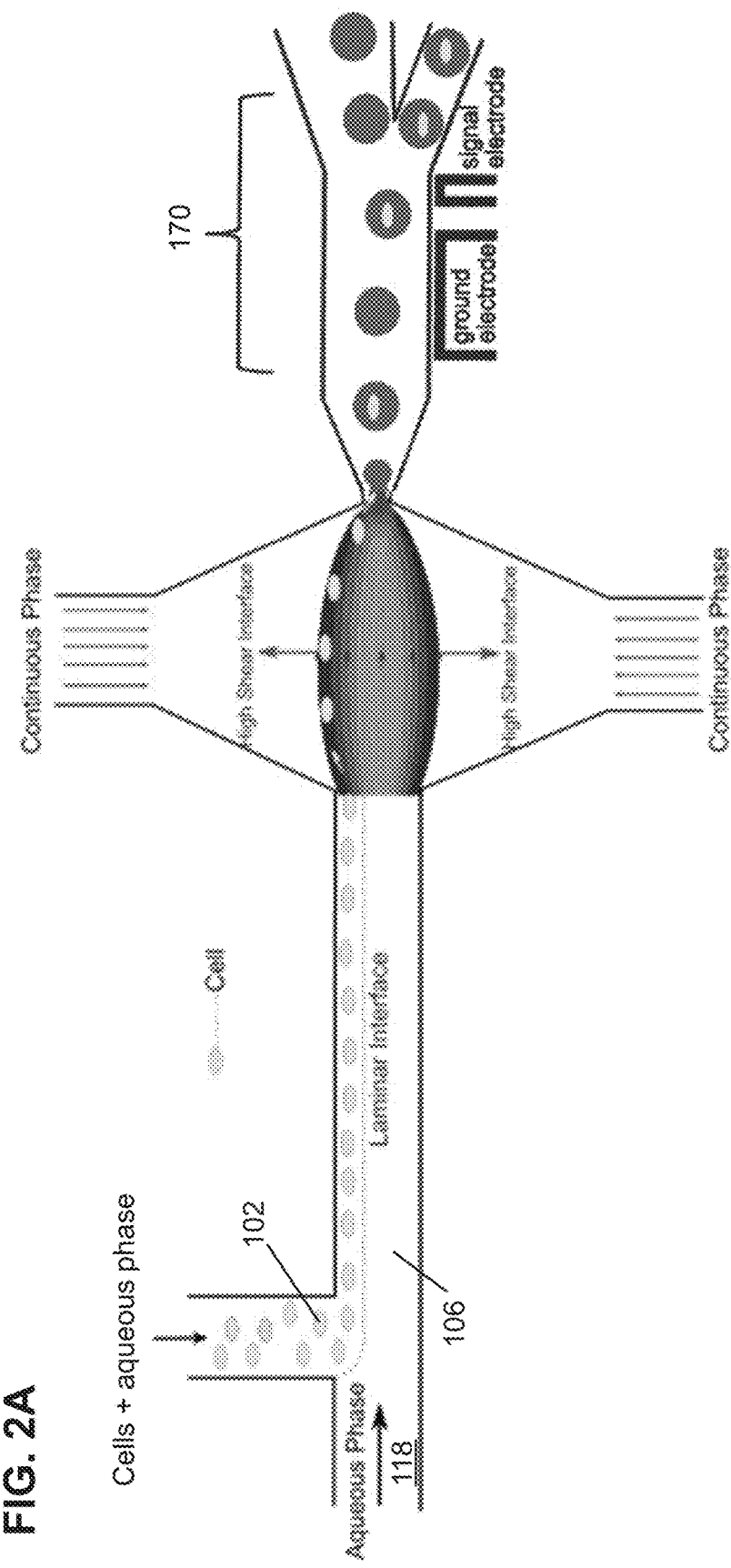
FIG. 2A shows another schematic illustration of high efficiency single cell indexing in droplets (1-1). Cells introduced from one inlet self-assemble along the channel wall while moving toward the high shear interfaces. At the droplet generation junction, the cells get pulled toward the high shear interfaces resulting in 1-1 encapsulation. The sorting module is incorporated downstream to sort out empty droplets from the single cell droplets. A dielectrophoresis (DEP) sorting module is shown as a non-limiting example.
Figure 2B:
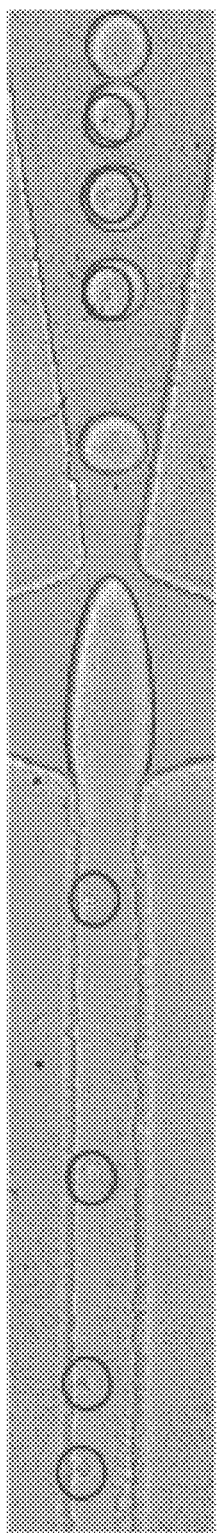
FIG. 2B shows 1-1 cell encapsulation in droplets of cells introduced from a single inlet. The circles indicate the single cells.

Alternatively, FIG. 2A is another embodiment of a microfluidic device that is configured to encapsulate a single cell in a single droplet. In contrast to the device depicted in FIG. 1A, the device of FIG. 2A has only two incoming microfluidic channels instead of three. Samples dispersed in a first fluid (e.g., water) is introduced through a first microfluidic channel and the first fluid is introduced through the through a second microfluidic channel. Laminar flow is established in the combining channel such that the cells self-assemble along the channel wall. By controlling the pressure ratio between the dispersed phase and the continuous phase, the concentration of samples in the dispersed phase and the droplet size, encapsulation of a single sample in a single droplet can be achieved as shown in the droplets of FIG. 2B.

Figure 3A:
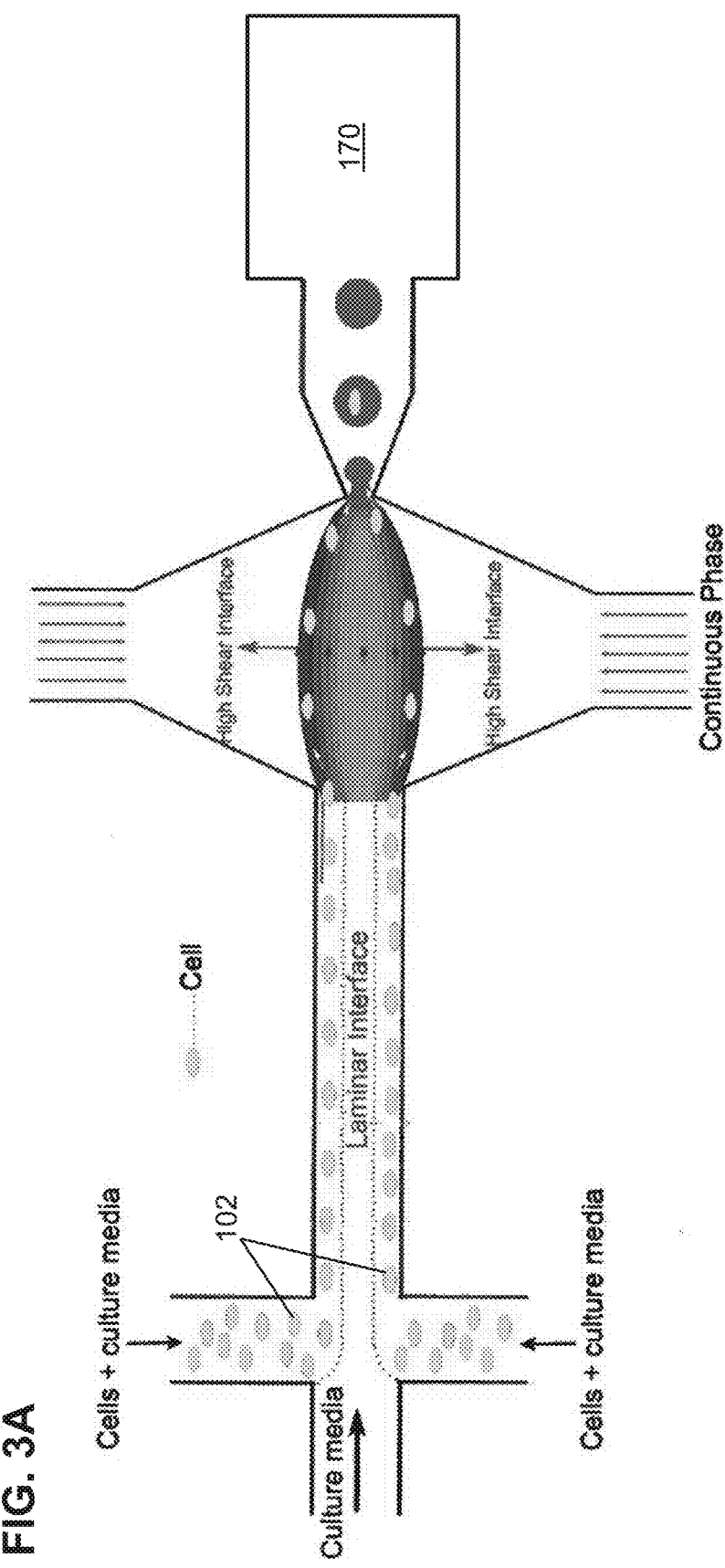
FIG. 3A is another schematic illustration of high efficiency single cell indexing in droplets (1-1). Cells introduced from two inlets self-assemble along the channel walls while moving toward the high shear interfaces. At the droplet generation junction, the cells get pulled toward the high shear interfaces resulting in 1-1 encapsulation. The sorting module is incorporated downstream to sort out empty droplets from the single cell droplets.
Figure 3B:
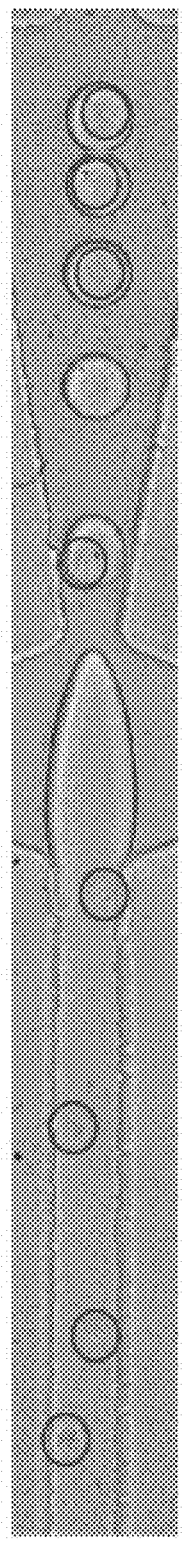
FIG. 3B shows one cell encapsulation in droplets of cells introduced from two inlets. The circles indicate the single cells.

It is noted that cells can be introduced through both the microfluidic channels. For example, as shown in FIG. 3A, samples can be introduced through both the first and the second incoming channels. In such embodiments, the pressure ratio between the dispersed phase and the continuous phase can be adjusted to change the size of the generated droplets to facilitate encapsulation of a single sample in a single droplet, as shown in the droplets of FIG. 3B.

In various embodiments, the size of the generated droplets can be tuned by adjusting the droplet generation regimes. The encapsulation of a single cell in a single droplet and/or a single bead and a single cell in a single droplet can be achieved in both geometry-mediated and dripping regimes. For example, when the droplets are generated in the geometry-mediated regime, the size of the droplet can be greater than or equal to the size of orifice diameter. In the dripping regime, where the droplet break-off occurs due to interfacial instability, the droplet size can be less than the size of the orifice. In both regimes, the beads and cells that assemble in single row along the channel wall are pulled into the droplets by the symmetrical high shear zone resulting in encapsulation. The droplet size can be tailored to the size of the incoming cells and/or concentrations by controlling the pressure and/or flow rate ratio between the dispersed phase and the continuous phase and the capillary number. Without wishing to limit the present invention, the encapsulation efficiency achieved using the methods described herein can be 30% or higher. More preferably, when combined with the sorting mechanism, the encapsulation efficiency achieved using the methods described herein can be about 80%. Further still, the present methods can be modified based on the desired application including single cell or bead encapsulation (1-1), and 1 cell-1 bead-1 droplet encapsulation or 1 cell-1 cell-1 droplet encapsulation (1-1-1) for different cell types and cell sizes.

EXAMPLES

The following are non-limiting examples of encapsulation using the interfacial shearing technique of the present invention. It is to be understood that the examples are for illustrative purposes only and are not intended to limit the present invention in any way. Equivalents or substitutes are within the scope of the invention.

Materials and Methods

The microfluidic devices were fabricated in polydimethylsiloxane (PDMS) using soft lithography. The PDMS molded imprints and another plain PDMS layer were plasma treated and brought together to form a permanent seal. The device was left in an oven at 120 ° C. overnight to regain its natural hydrophobicity. Ethyl oleate and 2% ABIL EM 90 formed the continuous phase, and mixture of water, lipids (DSPC and DSPE-PEG 2000), glycerol and surfactant (Pluronic F-68) form the dispersed phase. Hela cells and 10 μm beads were suspended in freshly prepared dispersed phase.

Both the continuous phase and the dispersed phase were introduced into the microfluidic chip using a constant pressure source via high speed solenoid valves controlled by a custom-built lab view program. One-one-one encapsulation was monitored using a Nikon 100-S inverted microscope and recorded using a Phantom camera V-310. Image J software was used to analyze the videos frame by frame, and yield the encapsulation data.

FIG. 1D is a demonstration of the encapsulation of 10 μm beads and HeLa cells in droplets. Beads self-assemble along the top channel wall while HeLa cells align along the bottom wall while moving towards a symmetrical high shear zone. 1-1-1 encapsulation is achieved in droplets circled in red. Similar results were achieved using beads and K-562 cells. Referring to FIG. 3B, single cell encapsulation successfully demonstrated using K-562 human erythromyeloblastoid leukemia cells, entering from both inlets of the junction. 1-1 encapsulation is achieved in droplets circled in red. Initial concentration of cells is $2.4\times10^6$ cells/mL.

Figure 4A:
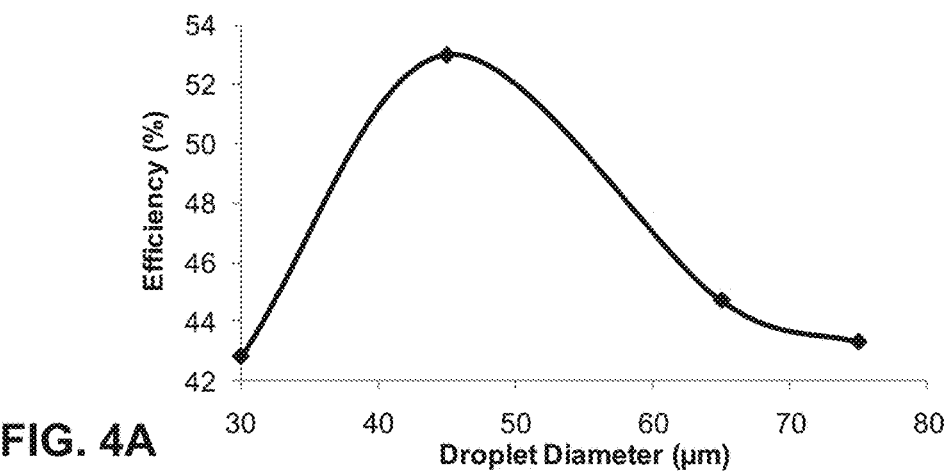
FIG. 4A is a graph of encapsulation efficiency vs. droplet diameter. The encapsulation efficiency increases with the droplet diameter, reaches a maximum, and decreases thereafter due to multiple encapsulations in one droplet.

FIG. 4A is a plot of 1-1 encapsulation efficiency vs. droplet diameter. A maximum of 53% is achieved at 45 μm.

Figure 4B:
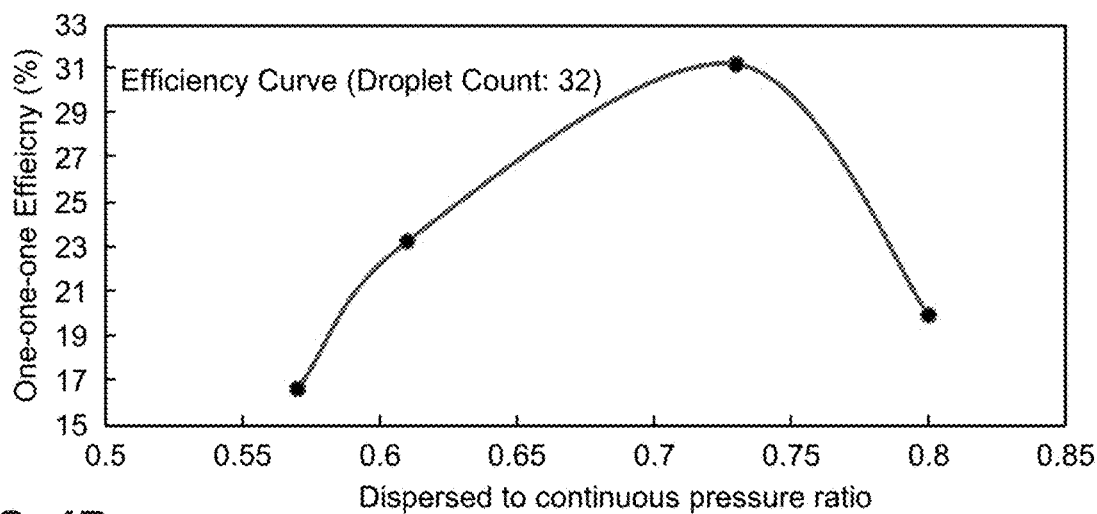
FIG. 4B is a graph of 1-1-1 encapsulation efficiency vs. pressure ratio of dispersed phase to continuous phase ($\varphi$). The encapsulation efficiency increases with the dispersed to continuous pressure ratio ($\varphi$), reaches a maximum, and decreases thereafter due to multiple encapsulations in one droplet.
Figure 4C:
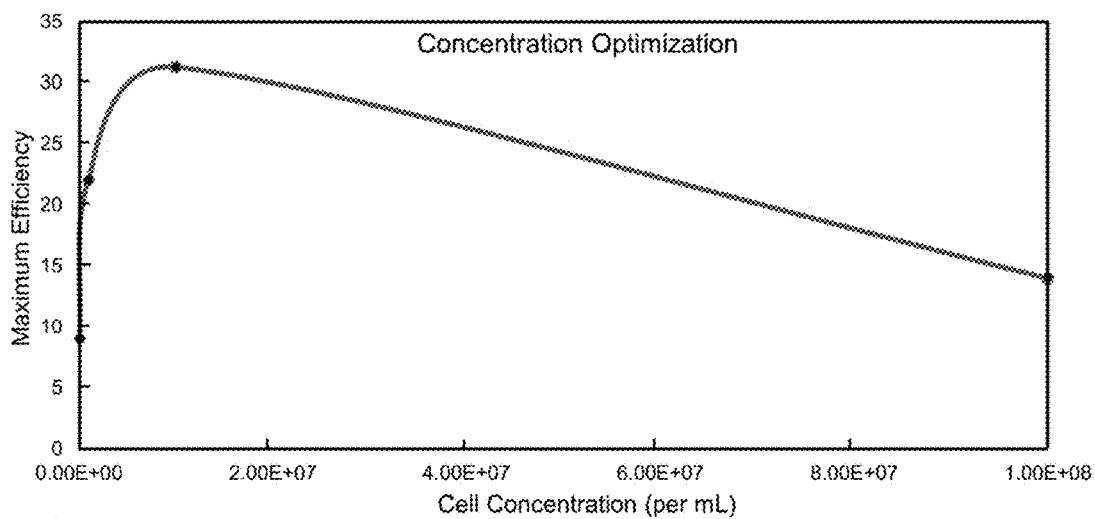
FIG. 4C is a graph of concentration optimization for encapsulation efficiency vs. cell concentration. The encapsulation efficiency increases with cell concentration, reaches a maximum, and decreases thereafter due to multiple encapsulations in one droplet.

FIG. 4B is a plot of 1-1-1 encapsulation efficiency vs. initial K-562 cell concentration, 10 µm bead concentration=1.3×$10^7$ beads/mL. A maximum of 31% is achieved at $10^7$ cells/mL. FIG. 4C is a plot of 1-1-1 encapsulation efficiency vs. the fluidic pressure ratio of the dispersed phase to continuous phase, showing a maximum of 32% at 0.73. K-562 cell concentration=$10^7$ cells/mL. 10 µm bead concentration=1.3×$10^7$ beads/mL. Dispersed phase pressure was held at constant 0.8 psi. Continuous phase pressure varied 1.0-1.4 psi.

The droplet diameter can be tuned by adjusting the flow rate ratio to achieve maximum encapsulation efficiency. By arranging the cells/beads single file along the channel wall using laminar flow, along with the high shear interface, the randomness involved in the encapsulation process is overcome to a considerable extent. Based on the examples described herein, the present invention has been demonstrated to perform one-one or one-one-one encapsulation in droplets utilizing the combined effect of laminar flow and high shear liquid-liquid interface at the microfluidic junction. These results suggest that this technique can be applied to droplet-based high-throughput genomic workflows.

Structures For Particle Spacing

Droplet-based microfluidics enables compartmentalization of the chemical ingredients and cells of interest in a microenvironment while avoiding contamination. This capability of precise manipulation of the fluid at the cellular length scale has revolutionized the single cell analysis methods. Nevertheless, the number of cells encapsulated per droplet in these systems is dictated by Poisson statistics, reducing the proportion of droplets that contain the desired number of cells and thus the effective rate at which single cells can be encapsulated.

Passive techniques may be implemented to control the number of cells per droplet. Among deterministic passive single cell encapsulation methods to overcome the random distribution of the cells and thus Poisson distribution limitations is inertial ordering of the cells prior to encapsulation. This method is limited due to difficulty of preparing high density cell solutions and preventing them from aggregating in long microchannels required for inertial ordering. Another method is closely packing of gel particles prior to encapsulation so that they are released at a constant rate. However, this method has limited applicability to the cells since they are more likely to clog the channels if they are present in high concentrations. Another technique is continuously focusing cells and microparticles using inertial lift force and vorticity (generated due to topographic pattern of the microchannel) via multi-orifice microchannels.

The microfluidic devices of the present invention incorporate a passive cell/microparticle focusing technique to beat the Poisson distribution limitations based on hydrodynamic and hydrophoresis phenomena. In one embodiment, a microfluidic device may comprise expansion-contraction regions (135) in the z-direction (channel height direction) disposed on the microchannels, such as the inlet channels or combining channel. As shown on FIGS. 5A-5B, a non-limiting example of the expansion-contraction region is herringbone structures (135) and regions without herringbone structures. The topographic pattern of the microchannel causes the particles to follow a specific streamline determined by a unique combination of helical flow, buoyant and gravitational forces. Thus, if the particles suspension is homogenous, the particles will all be focused in one streamline. For this purpose, two different variations of the herringbone structure may be used to improve focusing efficiency in different flow conditions (i.e. Reynolds number, particle concentration, etc.).

Figure 5A:
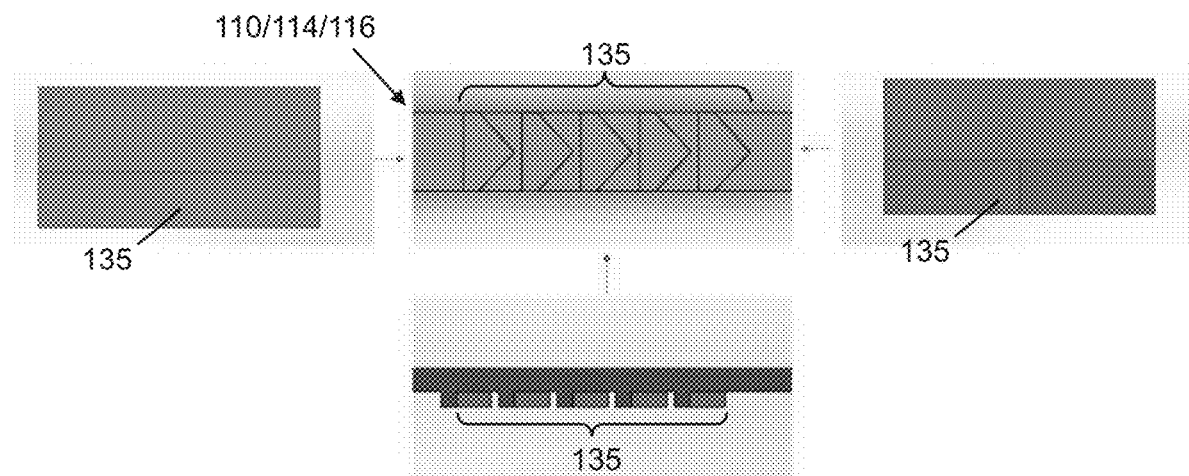
FIG. 5A shows top, side, back (left) and front (right) views of regular herringbone structures in a focusing/spacing microchannel.
Figure 5B:
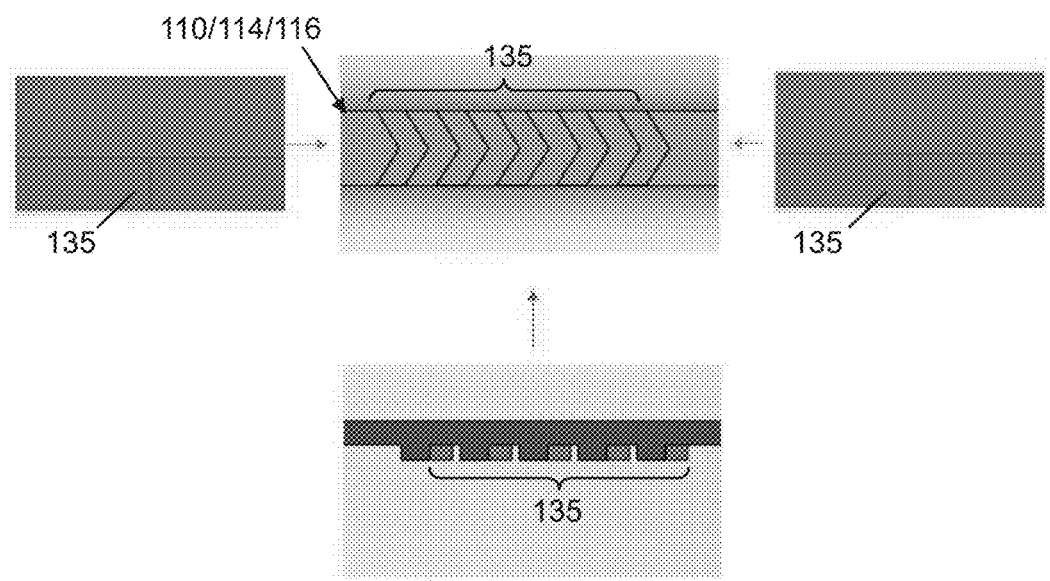
FIG. 5B shows top, side, back (left) and front (right) views of reduced-deviation flow herringbone structures in a focusing/spacing microchannel.

In one embodiment, the microchannel may comprise regular herringbone/chevron structures (135) as shown in FIG. 5A. In another embodiment, the microchannel may comprise reduced-deviation flow herringbone structures (135) as shown on FIG. 5B. The difference between the two embodiments is the angle of the tail of the herringbone structure has been reduced to 0° in FIG. 5A. The working principles of these two structures is as follows: when fluid and particles approach the apex (point) of the herringbone structure, they encounter a lateral (x-direction, toward channel walls) pressure gradient, the apex being a low-pressure region fluid and particles experience a focusing flow (toward the apex). This focusing flow concept is the same in both designs. In case of FIG. 5A, when particles and fluid escape from the herringbone structure, there is gradual decrease of the height depending on the tail angle of the herringbone structure. Due to the gradual height decrease, there is a pressure drop in the x-axis direction (channel wall direction) which causes the deviation flow (defocusing of the particles). In the embodiment of the FIG. 5B, once the fluid and particles escape from the proposed herringbone structure, there is a sudden contraction in the height of the channel and this will induce a pressure gradient in the vertical direction (channel height direction) rather than the lateral direction, minimizing the deviation of the particles from the focusing streamline when escaping the structure at high flow rate conditions.

Figure 6A:
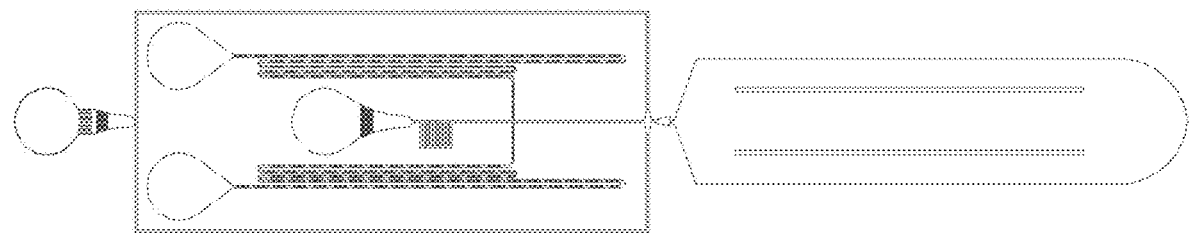
FIG. 6A shows a non-limiting embodiment of a high efficiency cell encapsulation microfluidic platform with spacing structures.
Figure 6B:
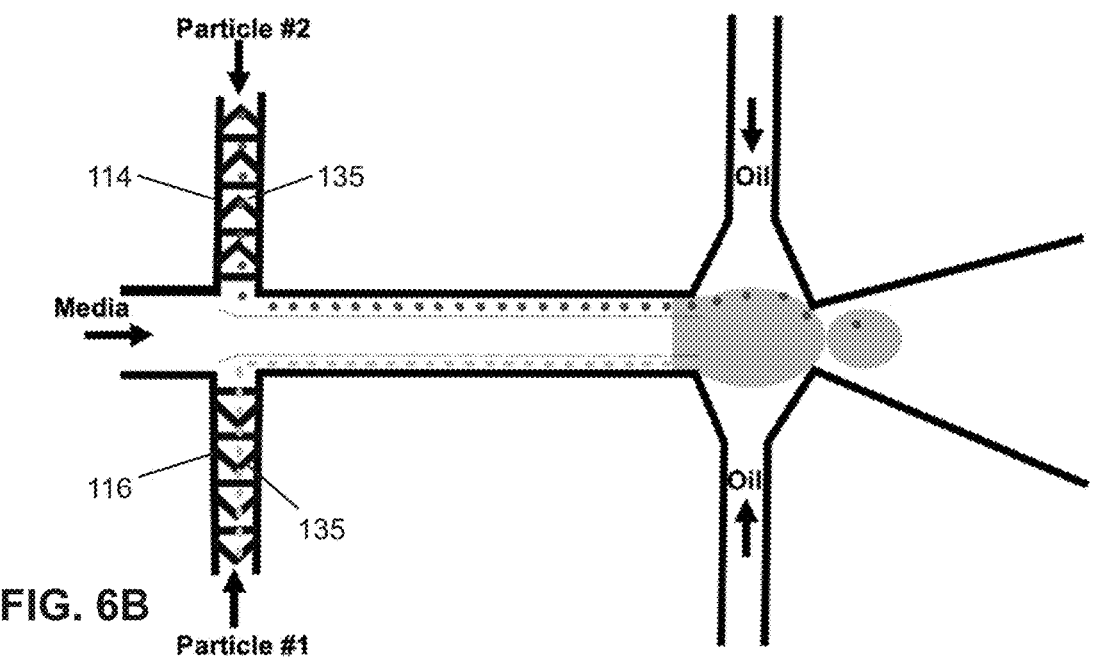
FIG. 6B is a top view of herringbone structure pattern integrated into the particle inlet channels.

Referring to FIG. 6B, in one embodiment, the focusing/spacing unit can be incorporated into the particle inlet channels (114, 116). Particles are ordered and spaced before entering the combining channel by flowing through a sequence of herringbone structures. Inside the combining channel, the sheath flow pushes particles along the wall while moving toward the high shear interface. At the droplet generation junction, both types of particles get pulled towards the high shear interface symmetrically from both channel boundaries, resulting in one particle of each type encapsulated in a droplet. Particles can be one cell and one barcoded bead to facilitate high efficiency single cell indexing (>30%), or both particles can be cells of different types to facilitate high fidelity cell-cell interaction studies. This type of encapsulation is termed "1-1-1" encapsulation. Media can be replaced with lysis buffer to lyse cells within droplets for gene sequencing applications.

Figure 6C:
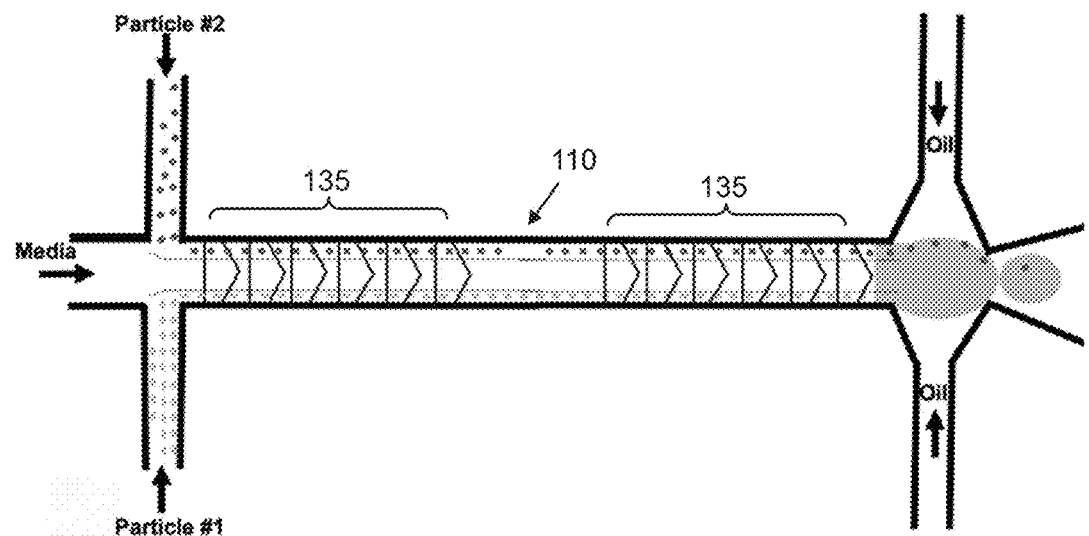
FIG. 6C shows the focusing/spacing herringbone structures integrated into the combining channel.

Referring to FIG. 6C, another variation in which this focusing/spacing unit can be incorporated is inside the combining channel (110) as opposed to the particle inlet channel. This way, particles can focus in a single streamline due to the presence of the laminar sheath flow which further assists the focusing effect of the herringbone structures. The zones with and without herringbone structures (expansion-contraction regions in Z-direction) help to focus and order the cells/beads as they move along the droplet junction, while sheath flow forces the particles to focus in a single streamline. At the droplet generation junction, both types of particles get pulled towards the high shear interface symmetrically from both channel boundaries, resulting in one particle of each type encapsulated in a droplet. Although not shown, in other embodiments, the spacing structures may be incorporated in both the inlet channels and combining channels. As compared to FIG. 6B, the direction of the herringbone structures in FIG. 6C is opposite with respect to flow for equilibrium focusing position of the cells. In FIG. 6B, the particles are focused to the middle of the channel or toward the apex of the herringbone structure, whereas in FIG. 6C, each particle stream is focused to the side of the herringbone structure, and not the apex of the structure, so that the two particle streams remain separate before encapsulation inside the droplets.

The random distribution of cells and beads when they are first introduced to the device inlet limits the encapsulation efficiencies of both 1-1 (a single cell inside a droplets) and 1-1-1 (a single cell and a single bead inside a droplet). By integrating the passive focusing and spacing technique with the encapsulation device (FIG. 6A), the encapsulation efficiencies may be increased. The hydrophoretic phenomenon depends on the channel dimension, particle size, flow conditions and the herringbone structure geometry. By carefully selecting the parameters, desired focusing of the particles can be achieved prior to or after entering the combining channel (sheath flow channel). By strategically choosing the particle concentration and flow rates (which affect droplet generation frequency and droplet diameter), both high efficiency 1-1 and 1-1-1 encapsulation can be achieved. Further still, the number of multiple encapsulation incidents can be reduced.

Droplet Sorting

In some embodiments, the sorting module (170) can direct droplets containing samples into one or more collection channels, and droplets into a waste collection channel, as shown in FIGS. 8A-10C. For example, the sorting module (170) directs droplets containing samples into a first collection channel. The first collection channel may be further divided into a plurality of sub-collection channels. A second sorting module (170) may be operatively coupled to the first collection channel, which directs the sample droplets into a specific sub-collection channel based on sample type or droplet size.

In some embodiments, the sorting module (170) may comprise one or more electrodes that sort the droplets (104) by dielectrophoresis (DEP). In DEP, droplets are manipulated in non-uniform electric fields. The movement of droplets in DEP is based on the difference in polarizability between the droplets and the surrounding medium. The droplets carry electrical potential, and respond uniquely to the different frequencies. A non-uniform AC electrical field manipulates the motion of droplets by creating a polarisability gradient between the droplets and the suspending medium. When the droplets are exposed to this non-uniform electric field, two different forces occur between the droplets and surrounding medium leading to a resultant force that moves the droplet.

In other embodiments, the sorting module (170) may comprise a lateral cavity acoustic transducer (LCAT) that that sort the droplets (104) by LCAT sorting. Briefly, LCAT devices exploit the phenomenon of acoustic micro-streaming to manipulate fluid flow and suspended cells/particles within a microfluidic environment. Bubble-induced acoustic micro-streaming develops when bubbles trapped within a liquid phase oscillate when excited by a sound field. As described in US20140011291A1, the specification of which is incorporated herein in its entirety, a dead-end side channel or LCAT, which has a gas contained therein, is coupled to the outlet channel at the junction of the collection channels. A transducer is configured to apply an external source of acoustic energy. Actuation of the transducer effectuates symmetrical oscillation of a gas/liquid boundary at the junction. For instance, when the LCAT is in the OFF state, particles flow through to one collection. When the LCAT is in the ON state, the particles are deflected into another collection channel by the oscillation.

FLIM Technique

The droplet-based microfluidic device of the present invention enables multiple types of high fidelity single cell studies (i.e. genotype, phenotype, and identification of other subcellular constituents). Combining this lab-on-a-chip microfluidic device with phasor FLIM enables noninvasive, label-free analysis of metabolism, secretion, and/or signaling at single cell resolution. Without wishing to limit the present invention to a particular theory or mechanism, the phenotype of cells assessed by FLIM can be correlated with the genotype of cells by droplet sequencing (drop-seq) or droplet digital PCR (ddPCR).

As previously described, high efficiency encapsulation can be achieved by strategically selecting the input particles (i.e. cells, beads), particle concentration, droplet size, and flow rates (which affect droplet generation frequency). Encapsulation efficiency depends on the cell concentration, droplet generation frequency and droplet diameter. Efficiency also varies with the flow rates of the dispersed and continuous phases, which are directly related to the in-channel fluidic pressure exerted by these phases.

In some embodiments, the present invention includes a FLIM microscopy system that can be used for FLIM analysis of droplets in a microfluidic chip. In one embodiment, the FLIM microscopy system may be made smaller and more portable. In another embodiment, the FLIM microscopy system is not integrated on the microfluidic chip. Downstream FLIM analysis may be used to characterize metabolic differences between proliferating and quiescent cells—a critical step towards label-free single cancer cell dormancy research. Media can be replaced with lysis buffer to lyse cells within droplets for gene sequencing applications.

Figure 11A:
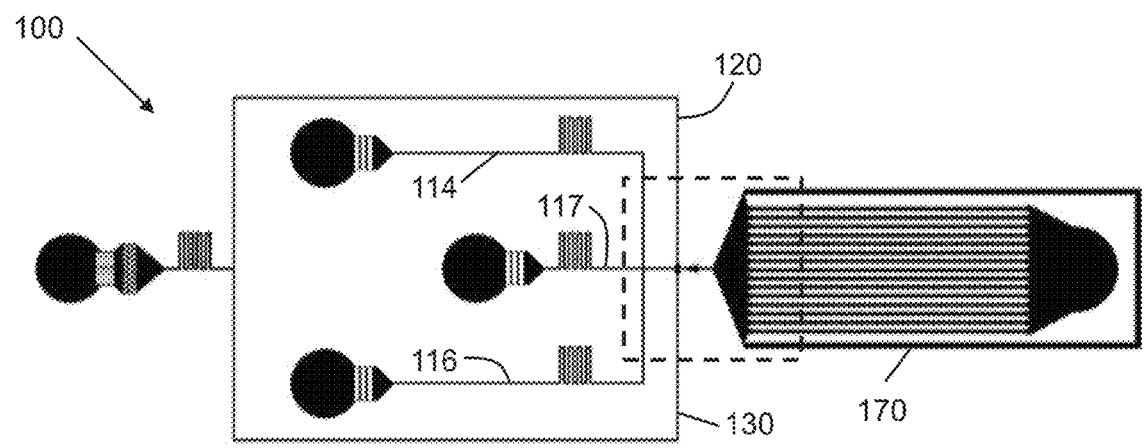
FIG. 11A shows a schematic of high efficiency cell encapsulation and indexing microfluidic platform which can encapsulate up to two distinct particles in a single droplet for downstream analysis via phasor FLIM.
Figure 11B:
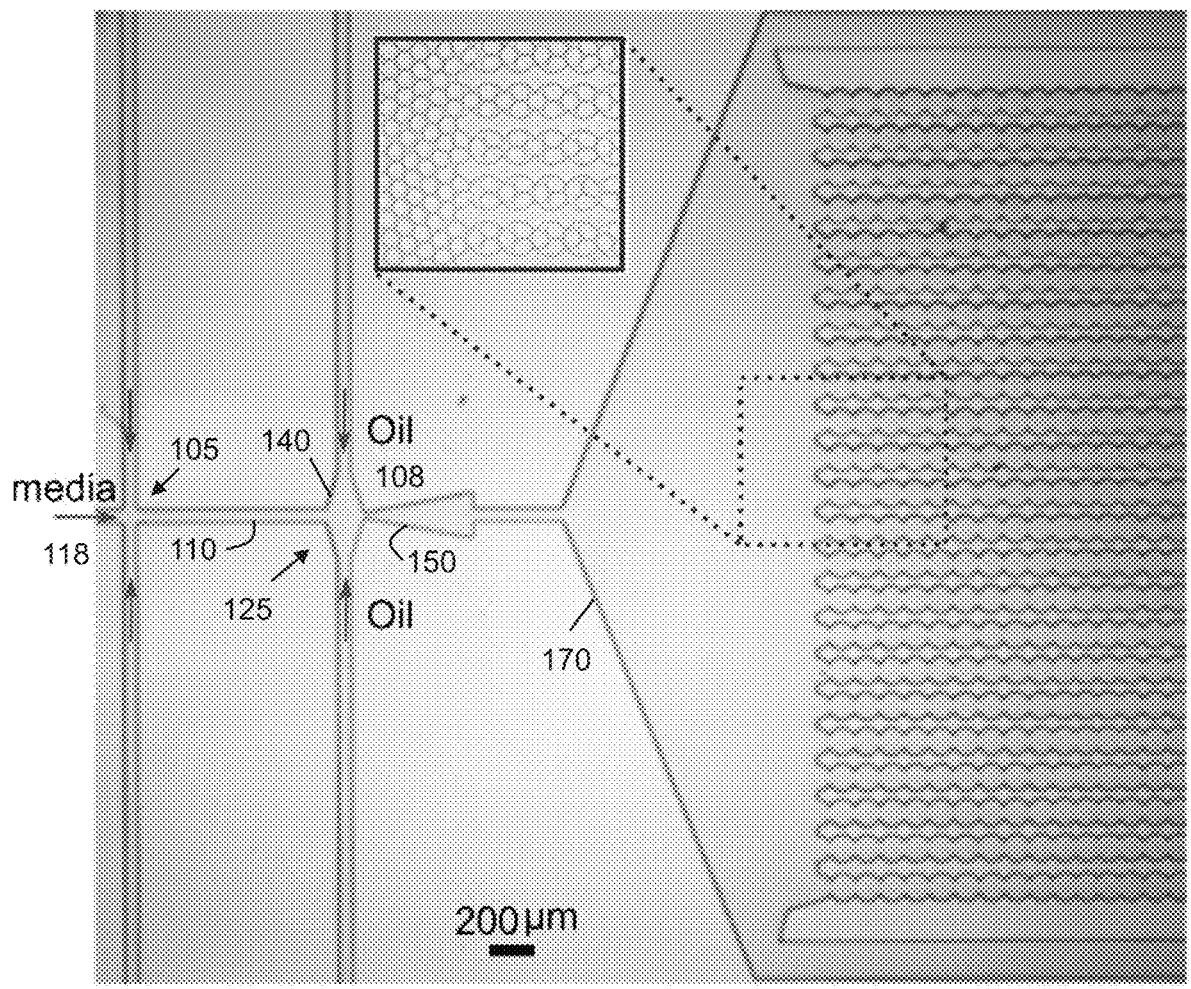
FIG. 11B is a top view, close-up photo of a selected region in FIG. 11A. Inset shows actual droplets held in place via a scalloped channel design to facilitate better FLIM readout.

In some embodiments, a droplet collection chamber can also be designed to facilitate other post-encapsulation functions (such as PCR). For example, as shown in FIG. 11B, the output channel from the droplet shearing junction may be fluidly connected to a droplet collection chamber comprising scalloped channels that hold the droplets in place to facilitate better FLIM readout. Downstream sorting may also be incorporated with FLIM. In one embodiment, an outlet of the droplet collection chamber may be fluidly coupled to a sorting module for sorting the droplets.

The combination of droplet encapsulation and FLIM may be used in 1-1 encapsulation or 1-1-1 encapsulation. 1-1-1 encapsulation may comprise cell and one bar-coded bead per droplet or two cells of different cell types per droplet. 1-1 encapsulation is demonstrated in the following example.

Phasor FLIM Analysis of Single Cells Within Droplets

A droplet microfluidic device together with the phasor approach to FLIM enables two key single cell investigations in droplets: 1) Unambiguously determine cell heterogeneity within a diverse population of single cells encapsulated in droplets, when physical attributes alone (size, shape, etc.) are insufficient, and 2) Distinguish metabolic state of cells encapsulated in droplets.

Supporting evidence for these two claims is shown in FIGS. 12A-13C. First, human leukemia cells K562 erythromyeloid and Jurkat T-cell leukemia were used in cell heterogeneity experiments. These cells are similar in morphology but have distinct phasor-FLIM signatures. Second, the FLIM NADH metabolic fingerprint provides a novel, label-free, quantitative measure of cell metabolic activity. For these experiments, cells from human foreskin fibroblasts cell line were starved of nutrients (serum) for 24 h and 72 h and the phasor-FLIM signature of each condition was observed.

Figure 12A:
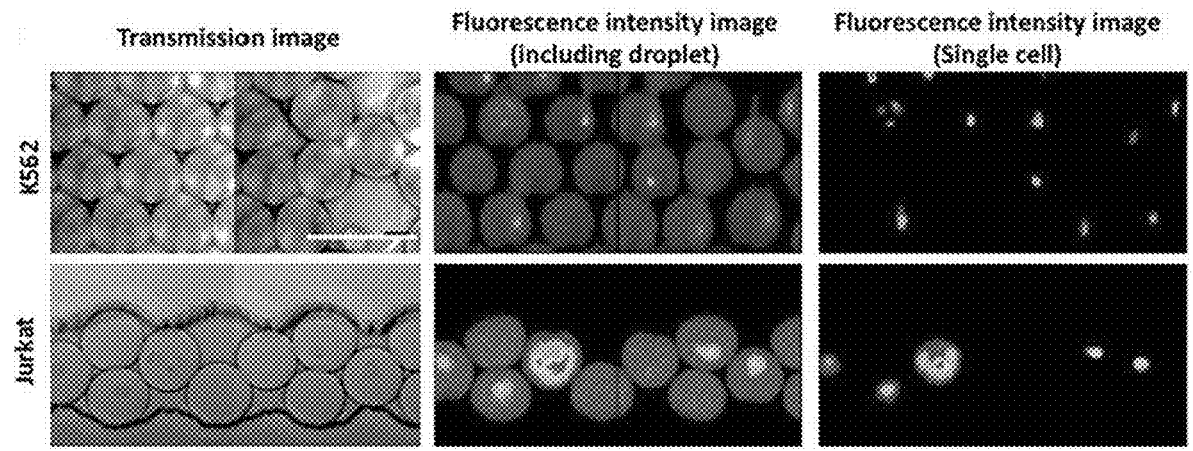
FIG. 12A shows transmission images and fluorescence intensity images of the K562 and Jurkat cells. Fluorescent images include the droplet (middle column) or only the encapsulated cell (right column). Scale Bar: 100 μm. The diameter of the K562 and Jurkat cells are 11.15 μm and 10.48 μm, respectively.
Figure 12B:
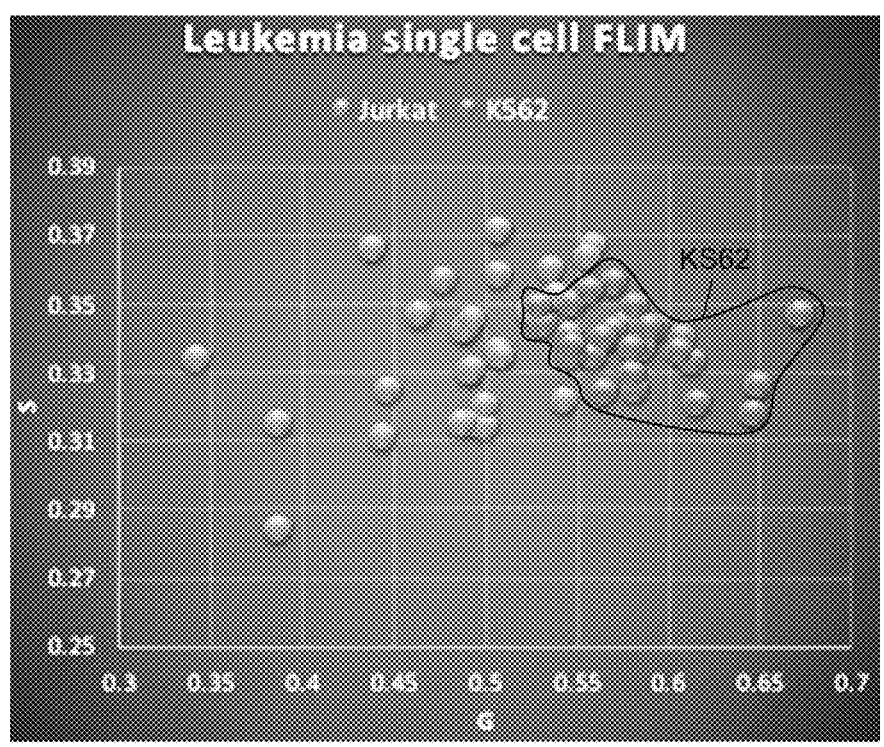
FIG. 12B is a scatter plot showing zoomed in phasor-FLIM results of the average s and g phasor values for encapsulated K562 (red) and Jurkat (blue) cells.

As shown in FIG. 12A, K562 and Jurkat cells cannot be distinguished based on morphology. However, the FLIM phasor data shows significant difference without any label. Separate FLIM images of the cells (not shown) were obtained via Ti-sapphire laser 740 nm excitation wavelength) and a commercial FastFLIM unit. The fluorescence lifetime information from each pixel of these FLIM images was transformed into one point in the phasor plot of FIG. 12B through Fourier transformation, in which the sine component of the fluorescence intensity decay curve of that pixel was transformed into its s axis coordinate, and the cosine component was transformed to its g axis coordinate in the phasor plot. The s phasor value ranges from 0-0.5 and the g phase value ranges from 0-1. The different leukemia cell lines K562 and Jurkat have significant difference in fluorescent phasor-FLIM signature. P value for g is 0.025 and for s is 0.0002.

Figure 13A:
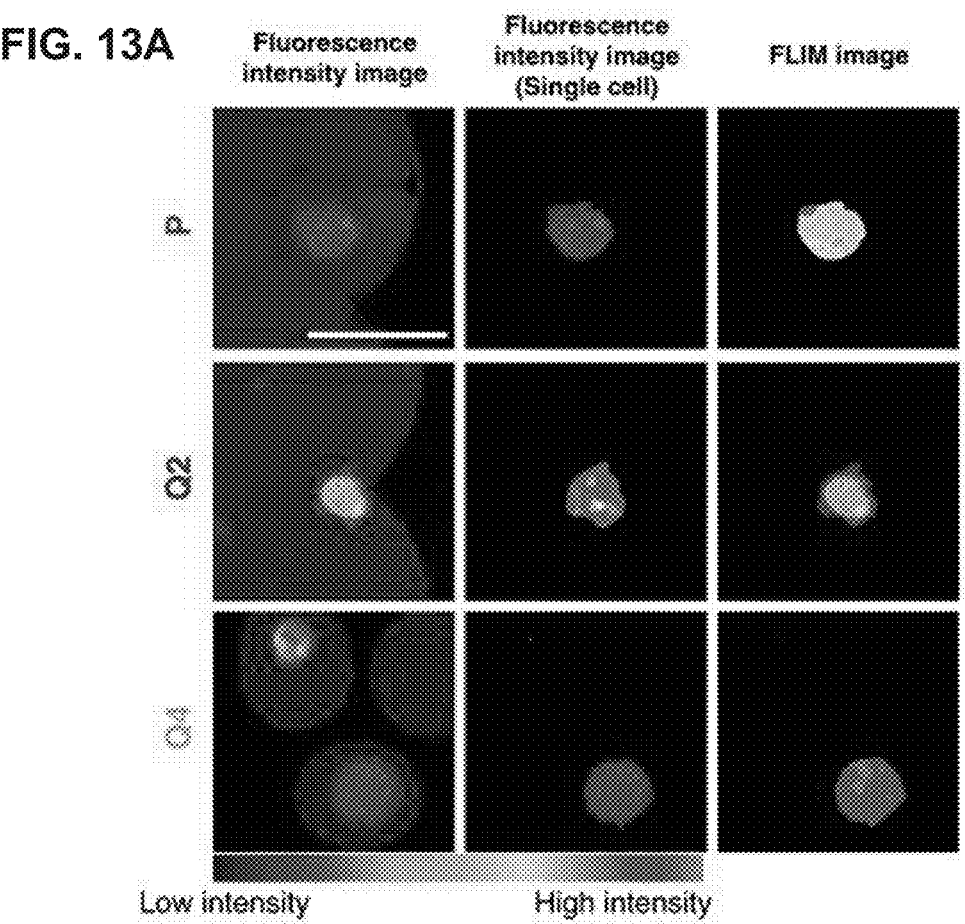
FIG. 13A shows fluorescence intensity images used to distinguish metabolic states of single human foreskin fibroblasts encapsulated in droplets (left column) and cell alone (middle column). FLIM images of the cell were also obtained under regular proliferation condition (P), serum starved for 2 days (Q2), and serum starved for 4 days (Q4). Scale bar=50 μm.
Figure 13B:
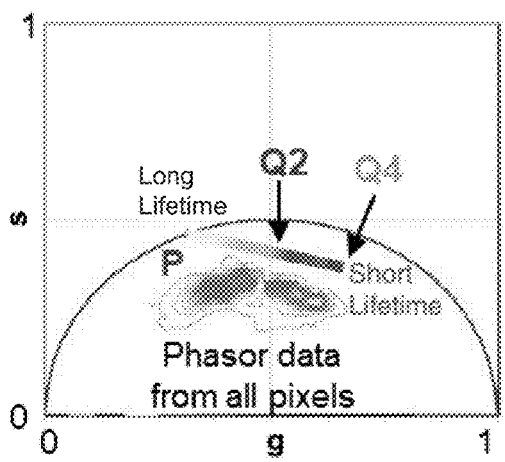
FIG. 13B is a phasor plot created through Fourier transformation of the FLIM lifetime decay data, in which the sine component of the fluorescence intensity decay curve of each pixel was transformed into its s axis coordinate, and the cosine component was transformed to its g axis coordinate in the phasor plot. The FLIM images of FIG. 13A were pseudo-colored using the color bar in FIG. 13B.
Figure 13C:
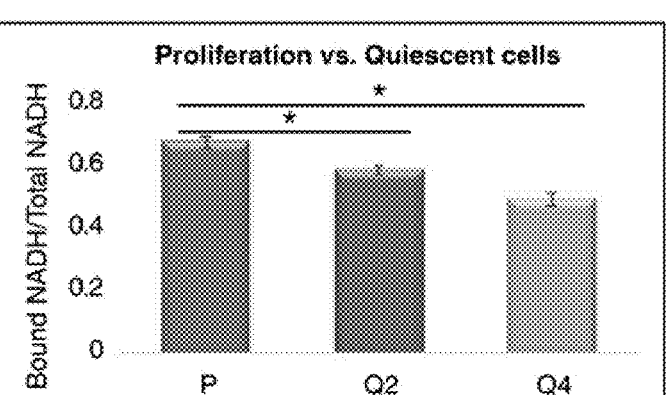
FIG. 13C is a bar graph showing the bound NADH/Total NADH ratio of the P, Q2, and Q4 conditions.

Referring to FIGS. 13A-13C, FLIM was used to distinguish metabolic states of single human foreskin fibroblasts encapsulated in droplets. FLIM data were acquired and processed by the SimFCS software developed at the Laboratory of Fluorescence Dynamics at UC Irvine. SimFCS can also produce color bars for easier visualization of the FLIM signature shifts resulting from metabolic changes. Phasor plot shows the FLIM signature distribution of the P, Q2, and Q4 conditions. From cyan to pink, the color shows the FLIM signature shift from the long lifetime (higher Bound/Free NADH indicating oxidative phosphorylation state) to the short lifetime (lower Bound/Free NADH indicating glycolytic state). As shown in FIG. 13C, the Q2 and Q4 groups show significant decreasing of Bound NADH, P value for P and Q2 groups is 0.001, P value for P and Q4 group is 0.002 (P group, n=21, Q2 group, n=4, Q4 group, n=19)

Existing methods for cell encapsulation in droplets are based on random encapsulation dictated by Poisson statistics. Efficiencies>50% for 1-1 encapsulation and >30% for 1-1-1 encapsulation have been achieved, a huge improvement over current encapsulation efficiency reported in the literature, which is typically about 1%. The present 1-1 and 1-1-1 encapsulation techniques significantly improve the efficiency of sample preparation for single cell genomics and proteomics (i.e. drop-seq and related applications). By combining with phasor FLIM analysis, a non-invasive, label-free, quick method to identify the cell's metabolic state is achieved, all within droplets. FLIM signatures also allow users to distinguish between various populations of cells, where size, shape, and other morphological features alone are not sufficient. Metabolic differences between proliferating and quiescent cells in droplets have been characterized. Once metabolic data is captured, the droplet containing the cell can be sorted downstream for further targeted analysis.

These capabilities can usher a new paradigm in single cell genomics, proteomics, and other "omic" analyses, as well as cell-cell interaction studies at fidelities. The combination of high efficiency cell encapsulation and FLIM suggests a powerful, droplet-based noninvasive and label-free method to distinguish individual cells based on their metabolic states, which could be used as an upstream phenotypic platform to correlate with downstream genomic statistics.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. The figures are understood to be representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for encapsulating a solid sample (102) in a droplet (104), comprising:
   a. providing a microfluidic device (100) comprising:
      i. a combining channel (110);
      ii. a first continuous phase channel (120) having a portion thereof disposed on one side of the combining channel;
      iii. a second continuous phase channel (130) having a portion thereof disposed on an opposite side of the combining channel, wherein said portions of the first and second continuous phase channels intersect at a terminal end of the combining channel to form an intersection region (140); and
      iv. an output channel (150) fluidly coupled to the intersection region (140);
   b. flowing a dispersed phase fluid (106) through the combining channel (110) at a first flow rate ($v_d$), wherein the dispersed phase fluid (106) comprises at least two flow streams (107), wherein one or both of said flow streams (107) comprises dispersed solid samples (102);
   c. adjusting $v_d$ of the dispersed phase fluid (106) to establish laminar flow in the combining channel (110) such that the solid samples (102) assemble near a sidewall (112) of the combining channel while flowing towards the intersection region (140);
   d. co-flowing a continuous phase fluid stream (108) through each of the first and second continuous phase channels (120, 130) at a second flow rate ($v_c$), wherein the continuous phase fluid streams (108) intersect the dispersed phase fluid (106) at the intersection region (140), wherein a droplet shearing junction (145) is formed within the intersection region (140) as the continuous phase fluid streams (108) merge with the dispersed phase fluid (106), wherein the droplet shearing junction (145) comprises an orifice (147) fluidly coupling the output channel (150) to the intersection region (140);
   e. adjusting $v_d$, $v_c$, or both such that each continuous phase fluid stream (108) forms a high shear interface (109) with the dispersed phase fluid (106) at the intersection region (140), wherein the solid samples (102) are drawn to the high shear interface (109) while flowing through the intersection region (140); and f. adjusting $v_d$, $v_c$, or both to generate droplets (104) encapsulating one solid sample (102) at the droplet shearing junction (145), wherein each droplet (104) is substantially sized to encapsulate said solid sample (102).

2. The method of claim 1, wherein the microfluidic device (100) comprises a first dispersed phase channel (114) comprising one of the flow streams (107) forming the dispersed phase fluid (106), and a second dispersed phase channel (116) comprising the other flow stream (107), wherein the first and second dispersed phase channels (114, (116) merge to form the combining channel (110).

3. The method of claim 2, wherein the microfluidic device (100) further comprises an aqueous phase channel (117) intersecting with the first and second dispersed phase channels (114, 116), wherein the aqueous phase channel (117) comprises aqueous phase fluid (118), wherein the aqueous phase fluid (118) flows in the combining channel (110) such that the aqueous phase fluid (118) forms a laminar interface stream (119) between the two flow streams (107).

4. The method of claim 2, wherein a plurality of spacing structures (135) are disposed in the dispersed phase channels (114, 116), the combining channel (110), or both for focusing the dispersed samples (102) in a streamline, wherein the plurality of spacing structures (135) create variations in channel height.

5. The method of claim 2, wherein the dispersed solid samples (102) are either cells or particles, wherein the dispersed solid samples (102) enter the combining channel (110) from one or both of the first and second dispersed phase channels, wherein one solid sample (102) is encapsulated as the droplet (104) is formed at the droplet shearing junction (145), wherein the droplet (104) encapsulating the one solid sample (102) is released from the orifice (147) into the output channel (150).

6. The method of claim 2, wherein the dispersed solid samples (102) comprises a plurality of cells flowing in one of the flow streams (107), and a plurality of particles flowing in the other flow stream (107), wherein when flowing through the combining channel (110), laminar flow of the dispersed phase fluid causes the cells to assemble near the sidewall (112a) and the particles to assemble near an opposing sidewall (112b), wherein at the intersection region (140), the cells are drawn to one high shear interface (109a) and the particles are drawn to the other high shear interface (109b), wherein one cell and one particle are co-encapsulated in one droplet (104) as said droplet (104) is formed at the droplet shearing junction (145), wherein the droplet (104) co-encapsulating the one cell and one particle is released from the orifice (147) into the output channel (150).

7. The method of claim 6, wherein the cells are eukaryotic cells, prokaryotic cells, or a combination thereof.

8. The method of claim 6, wherein the cells are animal cells, plant cells, algae cells, bacterial cells, fungal cells, protoplasts, pollen grains, microspores, or tetrads.

9. The method of claim 6, wherein the particles are beads.

10. The method of claim 1, further comprising sorting the droplets based on droplet content using a sorting module (170) operatively coupled to the output channel (150), wherein the output channel (150) is divided into a plurality of collection channels (154), wherein the sorting module (170) directs the droplets into a specific collection channel (154) based on droplet content.

11. The method of claim 10, wherein the sorting module (170) comprises one or more electrodes that sort the droplets (104) by dielectrophoresis (DEP), or one or more lateral cavity acoustic transducers (LCATs) that that sort the droplets (104) by LCAT sorting, or a fluorescence-lifetime-imaging microscope (FLIM).

12. The method of claim 10, wherein the sample droplets co-encapsulate a cell, lysis buffer, and a bar-coded bead, wherein said sample droplets are sorted by the sorting module (170) for downstream RNA sequencing.

13. The method of claim 1 further comprising observing cell-cell interactions using fluorescence lifetime imaging microscopy (FLIM) to determine cell heterogeneity and to distinguish metabolic state of cells encapsulated in droplets.

* * * * *